United States Patent
Shriver et al.

(10) Patent No.: US 8,617,896 B1
(45) Date of Patent: Dec. 31, 2013

(54) EVALUATING MIXTURES OF LOW MOLECULAR WEIGHT HEPARINS BY CHAIN PROFILES OR CHAIN MAPPING

(76) Inventors: Zachary Shriver, Cambridge, MA (US); Daniela Beccati, Brighton, MA (US); Ishan Capila, Ashland, MA (US); Nur Sibel Gunay, Brookline, MA (US); Jennifer Ozug, Norwood, MA (US); Steve Wudyka, North Andover, MA (US)

( * ) Notice: Subject to any disclaimer, the term of this patent is extended or adjusted under 35 U.S.C. 154(b) by 19 days.

(21) Appl. No.: 13/529,662

(22) Filed: Jun. 21, 2012

Related U.S. Application Data

(63) Continuation of application No. 13/307,243, filed on Nov. 30, 2011, now Pat. No. 8,252,597, which is a continuation of application No. 12/878,922, filed on Sep. 9, 2010, now Pat. No. 8,076,149, which is a continuation of application No. 12/619,626, filed on Nov. 16, 2009, now Pat. No. 7,816,144, which is a continuation of application No. 12/011,436, filed on Jan. 25, 2008, now Pat. No. 7,790,466.

(60) Provisional application No. 60/886,735, filed on Jan. 26, 2007.

(51) Int. Cl.
*G01N 33/00* (2006.01)

(52) U.S. Cl.
USPC .............. 436/94; 436/161; 436/174; 210/656

(58) Field of Classification Search
USPC ............................ 436/94, 161, 174; 210/656
See application file for complete search history.

(56) References Cited

U.S. PATENT DOCUMENTS

| | | | |
|---|---|---|---|
| 4,692,435 A | 9/1987 | Lormeau et al. | |
| 5,389,618 A | 2/1995 | Debrie | |
| 6,617,316 B1 | 9/2003 | Mourier et al. | |
| RE38,743 E | 6/2005 | Debrie | |
| 7,083,937 B2 | 8/2006 | Sasisekharan et al. | |
| 7,585,642 B2 * | 9/2009 | Sasisekharan et al. | 435/13 |
| 7,790,466 B1 * | 9/2010 | Shriver et al. | 436/94 |
| 7,816,144 B1 | 10/2010 | Shriver et al. | |
| 7,968,082 B1 | 6/2011 | Shriver et al. | |
| 8,076,149 B1 | 12/2011 | Shriver et al. | |
| 8,101,733 B1 | 1/2012 | Shriver et al. | |
| 2002/0169143 A1 * | 11/2002 | Sasisekharan et al. | 514/54 |
| 2003/0203385 A1 | 10/2003 | Venkataraman et al. | |
| 2004/0265943 A1 | 12/2004 | Viskov et al. | |

(Continued)

FOREIGN PATENT DOCUMENTS

| | | |
|---|---|---|
| EP | 1580197 A1 | 9/2005 |
| EP | 1582531 A1 | 10/2005 |

(Continued)

OTHER PUBLICATIONS

Van Putten et al., Determination of low molecular weight heparin in clinical laboratory, Haemostasis, 1984, vol. 14, pp. 205-210.

(Continued)

*Primary Examiner* — Monique Cole
(74) *Attorney, Agent, or Firm* — Lando & Anastasi LLP

(57) ABSTRACT

Methods for analyzing mixtures of polysaccharides, for example heparin such as unfractionated heparin and enoxaparin are described. In some instances, the mixtures are analyzed using fast performance liquid chromatography (FPLC) and high liquid performance chromatography (HPLC), e.g., strong anion exchange HPLC.

4 Claims, 3 Drawing Sheets

(56) References Cited

U.S. PATENT DOCUMENTS

| | | |
|---|---|---|
| 2005/0119477 A1 | 6/2005 | Mourier et al. |
| 2005/0186679 A1 | 8/2005 | Viskov et al. |
| 2005/0215519 A1 | 9/2005 | Viskov et al. |
| 2005/0288252 A1 | 12/2005 | Nurcombe et al. |
| 2006/0024664 A1* | 2/2006 | Sasisekharan et al. ............ 435/4 |
| 2007/0065921 A1 | 3/2007 | Sasisekharan et al. |
| 2007/0098708 A1 | 5/2007 | Myette |
| 2007/0161073 A1 | 7/2007 | Sasisekharan et al. |
| 2007/0287683 A1 | 12/2007 | Shriver et al. |
| 2008/0009069 A1 | 1/2008 | Mourier et al. |
| 2011/0207919 A1 | 8/2011 | Beccati et al. |

FOREIGN PATENT DOCUMENTS

| | | |
|---|---|---|
| EP | 1586588 A1 | 10/2005 |
| WO | 9003791 A1 | 4/1990 |
| WO | 0129055 A2 | 4/2001 |
| WO | 03078960 A2 | 9/2003 |
| WO | 2004027087 A2 | 4/2004 |
| WO | 2005009040 A2 | 1/2005 |
| WO | 2005080438 A1 | 9/2005 |
| WO | 2005090411 A1 | 9/2005 |

OTHER PUBLICATIONS

Venkataraman et al., "Sequencing complex polysaccharides", Science, 1999, vol. 286, pp. 537-542.
Volpi et al., "Characterization of heparins with different relative molecular masses (from 11 600 to 1600) by various analytical techniques", J. of Chromatography, 1993, vol. 622, pp. 13-20.
Volpi et al., "Hyaluronic acid and chondroitin sulfate unsaturated disaccharides analysis by high-performance liquid chromatography and fluorimetric detection with dansylhydrazine", Analytical Biochem., 2002, vol. 277, pp. 19-24.
Vynios et al., "Advances in analysis of glycosaminoglycans: its applications for the assessment of physiological and pathological states of connective tissues", J. of Chromatography B, 2002, vol. 781, pp. 21-38.
Watt et al., "Comparison of ovine, bovine and porcine mucosal heparins and low molecular weight heparins by disaccharide analyses and 13C NMR", Carbohydrate Polymers, 1997, vol. 33, pp. 5-11.
Yoshida et al., "Analyisis of unsaturated disaccharides from glycosaminoglycuronan by high-performance liquid chromatography", Analytical Biochem., 1989, vol. 117, pp. 327-332.
"2.6.26. Test for anti-D antibodies in intravenous immunglobulin", Pharmeuropa, Jan. 2004, vol. 16, No. 1, pp. 121-122.
Alban et al., "Development of SPC-ELISA: a new assay principle for the study of sulfated polysaccharide-protein interactions", Journal of Biomolecular Screening, 2001, vol. 6, No. 6, pp. 393-400.
Ampofo et al., "Disaccharide compositional analysis of heparin and heparan sulfate using capillary zone electrophoresis", Analytical Biochemistry, 1991, vol. 199, pp. 249-255.
Araki et al., "Application of 2-aminopyridine fluorescence labeling in the analysis of in vivo and in vitro metabolism of dextran sulfate sodium by size-exclusion high-performance liquid chromatorgraphy", J. Chromatography B Biomed. Sci., 2001, vol. 753, No. 2, pp. 209-215.
Bianchini et al., "Few bicyclic acetals at reducing end of low-molecular-weight heparins: might they restrict specification of pharmacopoeia?" Pharmeuropa Scientific Notes, 2005, vol. 1, pp. 1-3.
Bianchini et al., "Variability of heparins and heterogeneity of low molecular weight heparins" Seminars in Thrombosis and Hemostasis, 2007, vol. 33, No. 5, pp. 496-502.
Cerny et al., "Preparation of 2-amino-1,6-anhydro-2,3-dideoxy-b-D-arabino-hexopyranose. 1H- and 13C-N.M.R. spectra of deoxy derivatives of 2-amino-1,6-deoxy-D-glucose and 2-amino-1,6-anhydro-2-deoxy-D-mannose", Carbohydrate Research, 1984, vol. 130, pp. 103-114.
Citizens Petition filed with the United Staes Food and Drug Administration by Aventis Pharmaceuticals Inc. on Feb. 19, 2003.
Citizens Petition Supplemental filed with the United Staes Food and Drug Administration by Aventis Pharmaceuticals Inc. on Feb. 12, 2004.
Da Col et at., "Characterization of the chemical structure of sulphated glycosaminoglycans after enzymatic digestion; Application for liquid chromatography-mass spectrometry with an atmospheric pressure interface", J. of Chromatography, 1993, vol. 647, pp. 289-300.
Dawes et al., "The measurement of heparin and other therapeutic sulphated polysaccharides in plasma, serum and urine", Thrombosis and Haemostasis, 1985, vol. 54, No. 3, pp. 630-634.
Desai et al., "Oligosaccharide composition of heparin and low-molecular-weight heparin by capillary electrophoresis", Analytical Biochem., 1993, vol. 213, pp. 120-127.
Desai et al., "Molecular weight of low molecular weight heparins by 13C nuclear magnetic resonance spectroscopy", Carbohydrate Research, 1994, vol. 255, pp. 193-212.
Ernst et al., "Direct evidence for a predominantly exolytic processive mechanism for depolymerization of heparin-like glycosaminoglycans by heparinase I", PNAS USA, 1998, vol. 95, pp. 4182-4187.
Fareed et al., "Generic low-molecular-weight heparins: some practical considerations" Seminars in Thrombosis and Hemostasis, 2004, vol. 30, No. 6, pp. 703-713.
Fareed et al., "Biochemical and pharmacologic heterogeneity in low molecular weight heparins. Impact on the therapeutic profile", Current Pharmaceutical Design, 2004, vol. 10, pp. 983-999.
Guerrini et al., "Low molecular weight heparins: structural differentiation by bidimensional nuclear magnetic resonance spectroscopy", Seminars in Thrombosis and Hemostasis, 2007, vol. 33, No. 5, pp. 478-487.
Guo et al., "The disaccharide composition of heparins and heparan sulfates", Analytical Biochem., 1989, vol. 176, pp. 96-104.
Hirano, "NMR study of 4-deoxy-a-L-threo-4-enohexopyranosyluronic acid (1®3)2-acetamido-2-deoxy-D-hexoses produced in the enzymic digestion of hyaluronate, chondroitin and chondroitin sulfates", Organic Magnetic Resonance, vol. 2, pp. 577-580.
Holzgrabe et al., "Quantitative NMR spectroscopy—Applications in drug analysis", Journal of Pharmaceutical and Biomedical Analysis, vol. 38, pp. 806-812.
Imanari et al., "High-performance liquid chromatographic analysis of glycosaminglycan-derived oligosaccharides", J. of Chomatography A, 1996, vol. 720, pp. 275-293.
International Search Report from International Application Serial No. PCT/US03/07208 dated Nov. 16, 2004.
Jeske et al., "Pharmacologic profile of certoparin", Exp. Opin. Invest. Drugs, 1999, vol. 8, No. 3, pp. 315-327.
Karamanos et al., "Ion-pair high-performance liquid chromatography for determining disaccharide composition in heparin and heparan sulphate", J. of Chromatography, 1997, vol. 765, pp. 169-179.
Kariya et al., "Disaccharide analysis of heparin and heparan sulfate using deaminative cleavage with nitrous acid and subsequent labeling with paranitrophenyl hydrazine", J. Biochem., 1998, vol. 123, No. 2, pp. 240-246, Tokyo.
Kinoshita et al., "Microanalysis of glycosaminoglycan-derived oligosaccharides labeled with a fluorophore 2-aminobenzamide by high-performance liquid chromatography: application to disaccharide composition analysis and exosequencing of oligosaccharides", Analytical Biochem., 1999, vol. 269, pp. 367-378.
Kuhle et al., "Pharmacokinetic study of tinzaparin in pediatric patients", Blood, 2002, vol. 100, No. 11, Abstract No. 3975.
Lamari et al., "Analysis of glycosaminoglycan-derived disaccharides in biologic samples by capillary electrophoresis and protocol for sequencing glycosaminoglycans", Biomedical Chromatography, 2002, vol. 16, pp. 95-102.
Lee et al., "Separation of reduced disaccharides derived from glycosaminoglycans by high-performance liquid chromatography", J. of Chromatography, 1981, vol. 212, pp. 65-73.

(56) References Cited

OTHER PUBLICATIONS

Lindhart et al., "Mapping and quantification of the major oligosaccharide components of heparin", Biochem. Journal, 1988, vol. 254, pp. 781-787.
Lindhart et al., "New methodologies in heparin structure analysis and the genereation of Lmw heparins", Heparin and Related Polysaccharides, 1992, pp. 37-47, ed. D.A. Lane et al., Plenum Press, New York.
Lindhart et al., "Oligosaccharide mapping of low molecular weight heparins: structure and activity differences", J. of Medicinal Chem., 1990, vol. 33, No. 6, pp. 1639-1645.
Malsch et al., "High-resolution capillary electrophoresis and polyacrylamide gel electrophoresis of heparins," Journal of Chromatography A, 1995, vol. 716, pp. 258-268.
Mascellani et al., "Characterization of di- and monosulfated, unsaturated heparin disaccharides with terminal N-sulfated 1,6-anhydro-b-D-glucosamine or N-sulfated 1,6-anydro-b-D-mannosamine residues", Carbohydrate Research, 2007, vol. 342, pp. 835-842.
Merchant et al., "Structure of heparin-derived tetrasaccharides", Biochem. Journal, 1985, vol. 229, pp. 369-377.
Militsopoulou et al., "Determination of twelve heparin- and heparan sulfate-derived disaccharides as 2-aminoacridone derivatives by capillary zone electrophoresis using ultrviolet and laser-induced flourescence detection", Electrophoresis, 2002, vol. 23, pp. 1104-1109.
Park et al., "Purification and characterization of heparin sulphate proteoglycan from bovine brain", Biochem. Journal, 1999, vol. 344, pp. 723-730.
Pervin et al., "Separation of glycosaminoglycan-derived oligosaccharides by capillary electrophoresis using reverse polarity", Analytical Biochem., 1994, vol. 221, pp. 182-188.
Rhomberg et al., "Mass spectrometric and capillary electrophoretic investigation of the enzymatic degradation of heparin-like glycosaminoglycans", PNAS, 1998, vol. 95, pp. 4167-4181.
Rice et al., "High-performance liquid chromatographic separation of heparin-derived oligosaccharides", Analytical Biochem., 1985, vol. 150, No. 2, pp. 325-331.
Ruiz-Calero et al., "Pressure-assisted capillary electrophoresis-electrospray ion trap mass spectrometry for the analysis of heparin depolymerised disaccharides", J. of Chromatogrphy A, 2001, vol. 914, pp. 277-291.
Ruiz-Calero et al., "Use of reversed polarity and pressure gradient in the analysis of disaccharide composition of heparin by capillary electrophoresis", J. of Chromatography A, 1998, vol. 828, pp. 497-508.
Saad et al., "Compositional analysis and quantification of heparin and heparan sulfate by electrospray ionization ion trap mass spectrometry", Anal. Chem., 2003, vol. 75, pp. 2985-2995.
Scapol et al., "Capillary electrophoresis of heparin and dermatan sulfate unsaturated disaccharides with triethylamine and acetonitrile as electrolyte additives", J. of Chromatography A, 1996, vol. 735, pp. 367-374.
Sundaram et al., "Rational design of low-molecular weight heparins with improved in vivo activity," PNAS, Jan. 21, 2003, vol. 100, No. 2, pp. 651-656.
Supplemental Partial European Search Report from European Application No. EP 037446289 dated Jul. 14, 2008.
Thanawiroon et al., "Liquid chromatography/mass spectrometry sequencing approach for highly sulfated heparin-derived oligosaccharides", J. of Biological Chem., 2004, vol. 279, No. 4, pp. 2608-2615.
Thanawiroon et al., "Separation of a complex mixture of heparin-derived oligosaccharides using reversed-phase high-performance liquid chromatography", J. of Chromatography A, 2003, vol. 1014, pp. 215-223.
Toida et al., "Structural differences and the presence of unsubstituted amino groups in heparan sulphates from different tissues and species", Biochem. Journal, 1997, vol. 322, pp. 499-506.
Toyoda et al., "Rapid and sensitive analysis of disaccharide composition in heparin and heparan sulfate by reversed-phase ion-pair chromatography on a 2 mm porous silica gel column", J. of Chromatography A, 1999, vol. 830, pp. 197-201.

\* cited by examiner

EVALUATING MIXTURES OF LOW MOLECULAR WEIGHT HEPARINS BY CHAIN PROFILES OR CHAIN MAPPING

This application is a continuation of U.S. Ser. No. 13/307,243, filed Nov. 30, 2011, allowed, which is a continuation of U.S. Ser. No. 12/878,922, filed Sep. 9, 2010 now U.S. Pat. No. 8,076,149, issued Dec. 13, 2011 which is a continuation of U.S. Ser. No. 12/619,626, filed Nov. 16, 2009 now U.S. Pat. No. 7,816,144, issued Oct. 19, 2010, which is a continuation of U.S. Ser. No. 12/011,436 filed Jan. 25, 2008, now U.S. Pat. No. 7,790,466, issued on Sep. 7, 2010, which claims priority to U.S. Provisional Application No. 60/886,735 filed Jan. 26, 2007, the contents of which is incorporated herein in its entirety.

The invention relates to methods of analyzing samples containing complex carbohydrates, e.g., low molecular weight heparins (LMWHs), e.g., most preferably enoxaparin. In particular, it relates to methods which use fast protein liquid chromatography (FPLC) and/or high performance liquid chromatography (HPLC), e.g., anion exchange HPLC, to analyze, control or monitor the production of LMWHs, particularly enoxaparin. It also relates to useful analytes and compositions which can be detected or prepared with the methods described herein.

BACKGROUND

Complex polysaccharides have been used as pharmaceutical interventions in a number of disease processes, including oncology, inflammatory diseases, and thrombosis. Examples of pharmaceutical interventions in this class are hyaluronic acid, an aid to wound healing and anti-cancer agent, and heparin, a potent anticoagulant and anti-thrombotic agent. Complex polysaccharides function primarily through binding soluble protein signaling molecules, including growth factors, cytokines and morphogens present at the cell surface and within the extracellular matrices between cells, as well as their cognate receptors present within this environment. In so doing, these complex polysaccharides effect critical changes in extracellular and intracellular signaling pathways important to cell and tissue function. For example, heparin binds to the coagulation inhibitor antithrombin III promoting its ability to inhibit factor IIa and Xa. Being able to identify and quantify the type and extent of chemical modification of a polysaccharide chain as a result of isolation and processing would be of benefit both from (1) a process control standpoint and (2) understanding biologically specific structure-function relationships.

SUMMARY

The analysis of a LMWH, e.g., enoxaparin, e.g., by FPLC and/or HPLC, e.g., anion exchange HPLC, can be used to evaluate starting materials, processes, intermediates and final products in the production of LMWHs, particularly enoxaparin. The presence, distribution, profile or amount of a structure or species described herein can be used in these evaluations.

By way of example, FPLC analysis of enoxaparin can resolve mixtures of saccharides having the same chain length, also referred to herein as size fractions, as well as relative distribution of the size fractions and a size fraction profile as shown in FIG. 2. The amount of each size fraction in a preparation can also be determined. Accordingly, a preparation can be evaluated by determining the presence, distribution, profile or amount of one or more size fractions, e.g., one or more disaccharide fraction, trisaccharide fraction, tetrasaccharide fraction, hexasaccharide fraction, octasaccharide fraction, decasaccharide fraction, dodecasaccharide fraction and tetradecasaccharide fraction, e.g., in an amount provided in Table Ia or Table Ib. The FPLC analysis can also be used, e.g., to determine the presence of one or more contaminant in the enoxaparin sample.

By way of further example, HPLC analysis, e.g., anion exchange HPLC, of a size fractionated pool of enoxaparin, namely a tetrasaccharide fraction, hexasaccharide fraction and octasaccharide fraction can resolve the species described in Tables II, III and IV. It can also provide the amount of the species in the treated preparation, e.g., the amount of a tetrasaccharide chain provided in Table V. Thus, a preparation can be evaluated by determining the presence, distribution or amount of one or more of the species in Tables II, III or IV, e.g., in an amount provided in Table V. Although the species in Tables II, III and IV are derived from enoxaparin, some, e.g., 1, 3, 4, 5, 6, 9, 10, 12, 13 (from Table II) will also occur in other LMWHs and can be used in the evaluation of other LMWHs.

Methods of analysis described herein can be combined allowing, e.g., characterization of a sample by evaluation of the presence of one or more mixtures of chains having the same chain length, the distribution or profile of one or more size fractions shown in FIG. 2, or the amount of one or more size fraction found in Table Ia or Table Ib and the presence, distribution or amount of a subject species found in Table II, III and/or IV.

Methods disclosed herein are useful for analyzing or processing a LMWH preparation, e.g., to determine whether to accept or reject a batch of a LMWH, e.g., enoxaparin, or to guide or control of a step in the production of a LMWH, e.g., enoxaparin.

The methods described herein can be used with LMWHs, and in particular enoxaparin. Enoxaparin is the preferred LMWH and the examples and much of the discussion is directed to enoxaparin. The methods described herein can, though, be applied to other LMWHs. In some cases the methods are directly applicable and in some one of ordinary skill in the art will appreciate that modifications may be needed and can institute those as guided by the art and this disclosure.

In one aspect, the invention provides a method of evaluating or processing a polysaccharide mixture, e.g., a LMWH preparation, e.g., an enoxaparin preparation.

The method includes:

providing an evaluation of a parameter related to a subject entity, e.g., a structure, specie or species, e.g., a chain, or size fraction or fractions described herein, e.g., a subject entity listed in Table Ia, Table Ib, Table II, Table III, Table IV, Table V or depicted in FIG. 2. Such parameters can include, or are a function of, the presence, relative distribution, profile or amount of a subject entity, e.g., a structure, chain and/or size fraction disclosed herein and, optionally, providing a determination of whether the value (e.g., a value correlated with absence or presence) determined for the parameter meets a preselected criteria, e.g., is present in the amount described herein or distributed or has a profile described herein, thereby evaluating or processing the mixture.

In a preferred embodiment, the method includes providing a comparison of the value determined for a parameter with a reference value, or values, to thereby evaluate the sample. In preferred embodiments, the comparison includes determining if the test value has a preselected relationship with the reference value, e.g., determining if it meets the reference value. The value need not be a numerical value but can be merely an indication of whether the subject entity is present.

In a preferred embodiment, the method includes determining if a test value is equal to or greater than a reference value, if it is less than or equal to a reference value, or if it falls within a range (either inclusive or exclusive of one or both endpoints). By way of example, the amount of a structure listed in Table II can be determined and, optionally shown to fall within a preselected range, e.g., a range which corresponds to a range A, B, C or D from Table V.

In preferred embodiments, the test value, or an indication of whether the preselected relationship is met, can be memorialized, e.g., in a computer readable record.

In preferred embodiments, a decision or step is taken, e.g., the sample is classified, selected, accepted or discarded, released or withheld, processed into a drug product, shipped, moved to a different location, formulated, labeled, packaged, released into commerce, or sold or offered for sale, depending on whether the preselected relationship is met. E.g., based on the result of the determination, or upon comparison to a reference standard, the batch from which the sample is taken can be processed, e.g., as just described.

As mentioned above, the methods disclosed herein can include evaluating the presence, distribution, profile or amount, of a selected subject entity, e.g., a structure or species, e.g., a selected chain, or a size fraction or fractions in a sample. Examples of a species, sometimes referred to herein as a chain, include di-, tri-, tetra-, hexa-, octa- (and so on) saccharides. A structure can be, e.g., a particular residue, or group of resides, e.g., a disaccharide pair, existing within a chain. Other examples of structures include selected intersaccharide linkages, terminal groups, epimeric forms, the presence or location of a derivative moiety, e.g., a sulfate or an acetyl group, an 1,6 anhydro structure, a $\Delta^{4,5}$ double bond uronic acid at the non-reducing end or odd-number chain length (hexosamine at the reducing end).

A particularly preferred species, with regard to Table Ia, Table Ib or FIG. 2, is a size fraction of tetrasaccharides, hexasaccharides, octasaccharides, decasaccharides or dodecasacchrides.

A particularly preferred structure e.g., with regard to Table II, III and IV, is a sulfate group, an acetyl group, a 1,6 anhydro structure, a $\Delta^{4,5}$ double bond at the non-reducing end, an anomeric state, a mannosamine or glucosamine at the reducing end, galacturonic acid, glucuronic acid or iduronic acid, and combinations thereof.

A particularly preferred species, with regard to Table II is a tetrasaccharide that includes five, six sulfate groups and/or 0 or 1 galacturonic acids and/or a mannosamine or glucosamine at the reducing end and/or a $\Delta^{4,5}$ double bond at the non-reducing end and/or 1,6 anhydro structure. Examples of preferred species include $\Delta U_{2S}H_{NS,6S}I_{2S}Man_{NS,6S}$, $\Delta U_{2S}H_{NS,6S}I_{2S}Man_{NS}(1,6)$, and $\Delta U_{2S}H_{NS,6S}I_{2S}H_{NS}(1,6)$.

A particularly preferred species, with regard to Table III is a hexasaccharide that includes eight or nine sulfate groups and/or one or no acetyl groups and/or 0 or 1 galacturonic acids and/or a mannosamine or glucosamine at the reducing end and/or a $\Delta^{4,5}$ double bond at the non-reducing end and/or 1,6 anhydro structure. Examples of preferred species include $\Delta U_{2S}H_{NS,6S}I_{2S}H_{NS,6S}GH_{NS,6S}$, $\Delta U_{2S}H_{NS,6S}I_{2S}H_{NS,6S}I_{2S}H_{NS}(1,6)$ and $\Delta U_{2S}H_{NS,6S}I_{2S}H_{NS,6S}I_{2S}Man_{NS}(1,6)$.

A particularly preferred species, with regard to Table IV is a octasaccharide that includes ten, eleven and twelve sulfate groups and/or 0 or 1 galacturonic acids and/or a mannosamine or glucosamine at the reducing end and/or a $\Delta^{4,5}$ double bond at the non-reducing end and/or 1,6 anhydro structure. Examples of preferred species include $\Delta U_{2S}H_{NS,6S}I_{2S}H_{NS,6S}I_{2S}H_{NS,6S}I_{2S}Man_{NS,6S}$ and $\Delta U_{2S}H_{NS,6S}I_{2S}H_{NS}GH_{Nac}$-LR.

The evaluation of the presence, distribution, profile, or amount of a subject entity, e.g., a structure, specie or species, size fraction or size fractions can show if the subject entity or a LMWH preparation, e.g., an enoxaparin preparation, meets a reference standard.

In preferred embodiments methods and/or compositions disclosed herein are useful from a process standpoint, e.g., to monitor or ensure batch-to-batch consistency or quality, or to evaluate a sample with regard to a reference, e.g., a preselected value.

In preferred embodiments, methods and compositions disclosed herein can be used to determine if a test batch of a LMWH, e.g., enoxaparin, can be expected to have one or more of the properties of the LMWH, e.g., enoxaparin. Such properties can include a property listed on the product insert of a LMWH, e.g., enoxaparin, a property appearing in a compendium, e.g., the US Pharmacopeia, or a property required by a regulatory agency, e.g., the FDA, for commercial use. A determination made by a method disclosed herein can be a direct or indirect measure of such a property. For example, a direct measurement can be where the desired property is a preselected level of component, e.g., species or structure, measured. In an indirect measure, the measured subject entity is correlated with, or is a proxy for a desired property, e.g., a property described herein.

Exemplary properties for enoxaparin include:

A preselected level of anti-XA activity, e.g., between 75-150 IU/mg and preferably about 100 IU/mg;

A preselected level of anti-IIA activity, e.g., between 20-35 and preferably about 30 IU/mg;

A preselected ratio of anti-XA/anti-IIA activity, e.g., between 3.3-5.3 and preferably about 4;

A preselected value for average molecular weight, e.g., between 4300-4800 Da and preferably about 4500 Da;

A set of preselected value for molecular weight distribution, e.g., about 12-20% and preferably 16% are <2000 Da species, greater than or equal to 68-82% and preferably greater than or equal to 68% are 2000-8000 Da species; and less than or equal to 18% are >8000 Da species;

A preselected level of chains ending in a 1,6-anhydro linkage, e.g., between 15-30% and preferably about 15-25% or 20-30%, e.g., as measured by weight average molecular weight or total percent chains;

A preselected value for the linkage region form, from 0.3-1.7 area %.

Methods and compositions disclosed herein can be used where the presence, distribution, profile or amount, of one or more structure, species, or size fractions in the mixture may possess or impinge on the biological activity.

The methods are also useful from a structure-activity prospective, to evaluate or ensure biological equivalence.

In a preferred embodiment, the sample is analyzed by FPLC. In a preferred embodiment, the method includes: providing an enoxaparin preparation; and subjecting the enoxaparin preparation to analysis, e.g., by FPLC, and optionally, evaluating the presence, distribution, profile or amount of a selected subject entity, e.g., a size fraction or size fractions with regards to FPLC analysis. A selected subject entity with regards to FPLC can include a low molecular weight fraction, e.g., a fraction eluted at about 0.76-0.81 CV (In this case, column volume: 462 ml) or a high molecular weight fraction, e.g., a fraction, at about 0.32-0.35 CV (In this case, column volume: 462 ml) that are indicative the absence, presence or amount of a contaminant in a sample.

In a preferred embodiment, the size fraction or size fractions is evaluated using, e.g., size exclusion chromatography with FPLC, e.g., carried out on a column having a molecular weight range of about 100 to 30,000, e.g., about 500 to 30,000; 500 to 20,000; 1500 to 20,000; 100 to 10,000; 100 to 8000; 100 to 7000. In one embodiment, the preparation is analyzed at wavelength of about 200 to 300 nm, e.g., 232 nm, over a run time of about 2 to 10 hours, e.g., 4 to 8 hours, e.g., 6 hours. Suitable running buffers can include, e.g., one or more of sodium chloride, sodium phosphate, disodium hydrogen phosphate dodecahydrate, ammonium acetate e.g., at a pH of about 5 to 8, e.g., 7.

In one embodiment, the LMWH, e.g., enoxaparin, preparation (e.g., the undigested LMWH, e.g., enoxaparin, preparation) includes one or more trisaccharide, tetrasaccharide, hexasaccharide, octasaccharide, decasaccharide, dodecasaccharide, tetradecasaccharide and combinations thereof.

In one embodiment, the method includes determining if one or more of a low molecular weight contaminant fraction; a fraction of trisaccharides; a fraction of tetrasaccharides; a fraction of hexasaccharides; a fraction of octasaccharides; a fraction of decasaccharides; a fraction of dodecasaccharides; a fraction of tetradecasaccharides; and a high molecular weight contaminant fraction, is present. Examples of low molecular weight contaminants include, e.g., contaminants associated with the manufacturing process such as monosaccharide degradants, commonly associated with color body formation. Examples of high molecular weight contaminants include, e.g., contaminants from the starting material (e.g., UFH) such as dermatan sulfate.

In one embodiment, the method includes identifying the distribution of one or more size fractions, e.g., trisaccharide, tetrasaccharide, hexasaccharide, octasaccharide, decasaccharide, dodecasaccharide, tetradecasaccharide preparation e.g., relative a different size fraction in the preparation.

In one embodiment, the method includes determining if one or more of the trisaccharide fraction, a tetrasaccharide fraction, a decasaccharide fraction, a dodecasaccharide fraction is present at a lower intensity than one or more of the hexasaccharide and octasaccharide fraction. In one embodiment, the tetrasaccharide fraction is present at a lower intensity than the hexasaccharide and/or octasaccharide fraction; the decasaccharide fraction is present at an intensity similar to or less than the octasaccharide fraction; the dodecasaccharide fraction is present at an intensity less than the decasaccharide, octasaccharide and/or hexasaccharide fraction.

In one embodiment, the size of fractions from an enoxaparin preparation is analyzed to determine if the tetrasaccharide fraction and the dodecasaccharide fraction are present at an intensity less than the decasaccharide, octasaccharide and hexasaccharide fraction and/or the decasaccharide at a similar or lower intensity than the octasaccharide and hexasaccharide fractions.

In one embodiment, the size fractions from an enoxaparin sample are analyzed to determine if it has a saw-tooth profile similar to or identical with the profile depicted in FIG. 2.

In a preferred embodiment, the method includes evaluating a subject entity to determine the amount of that entity in a sample. The amount can be expressed, e.g., in term of % area under the curve (AUC) or % height of the peaks.

In some embodiments, the amount of the subject entity is determined and then evaluated to determine if it is present in a preselected amount or range, e.g., an amount or range described herein, e.g., in Table Ia or Ib.

In one embodiment, a percentage of chains of a size fraction, e.g., the total percent of chains of a particular size fraction, in a preparation has been determined, e.g., by % AUC, or by % Height, and preferably the method includes determining or confirming that the percent of chains of that size fraction is in that range. In one embodiment, the range for a size fraction is one or more of the following:

TABLE Ia

Ranges are in Height %.

| Chain mapping by FPLC Distribution by Height % | Range A Height % | | Range B Height % | | Range C Height % | |
|---|---|---|---|---|---|---|
| Tetra- | 14.8 | 17.8 | 14.1 | 18.8 | 12.5 | 20.4 |
| Hexa- | 21.2 | 23.9 | 20.8 | 23.9 | 19.7 | 24.9 |
| Octa- | 21.6 | 22.7 | 21.5 | 22.8 | 21.1 | 23.3 |
| Deca- | 19.8 | 21.2 | 19.7 | 21.5 | 19.1 | 22.0 |
| Dodeca- | 17.6 | 19.3 | 17.3 | 19.6 | 16.5 | 20.3 |

TABLE Ib

Ranges are in Area %

| Chain Mapping by FPLC Distribution by Area % | Range A Area % | | Range B Area % | | Range C Area % | |
|---|---|---|---|---|---|---|
| Tetra- | 9.8 | 12.3 | 9.1 | 12.5 | 8.0 | 13.7 |
| Hexa- | 18.8 | 20.4 | 18.4 | 20.6 | 17.6 | 21.3 |
| Octa- | 16.8 | 17.4 | 16.6 | 17.5 | 16.3 | 17.9 |
| Deca- | 13.0 | 14.1 | 12.9 | 14.4 | 12.4 | 14.9 |
| Dodeca- and higher size chains | 34.0 | 38.8 | 33.4 | 39.9 | 31.3 | 42.0 |

In a preferred embodiment, the method includes providing a comparison of the value determined for a parameter with a reference value or values, to thereby evaluate the sample. In preferred embodiments, the comparison includes determining if the test value has a preselected relationship with the reference value, e.g., determining if it meets the reference value. The value need not be a numerical value but, e.g., can be merely an indication of whether the subject entity is present.

In a preferred embodiment, the method includes determining if a test value is equal to or greater than a reference value, if it is less than or equal to a reference value, or if it falls within a range (either inclusive or exclusive of one or both endpoints). By way of example, the amount of a structure listed in Table Ia and b can be determined and, optionally shown to fall within a preselected range, e.g., a range which corresponds to a range A, B, C from Table Ia and b.

In one embodiment, the method further includes determining the presence, distribution and/or quantity of at least two or more (e.g., 2, 3, 4, or 5) of the size fractions, e.g., the size fractions of Table Ia or Table Ib, in the preparation.

In a preferred embodiment, the sample is evaluated for the presence of each of the size fractions in Table Ia or Table Ib.

In a preferred embodiment, one or more structures from a subset of the size fractions in Table Ia and Table Ib are evaluated, e.g.:

one or more of structures tetra- and hexa- (as referenced in Table Ia or Table Ib);

one or more of structures tetra-, hexa- and octa- (as referenced in Table Ia or Table Ib);

one or more of structures hexa- and octa- (as referenced in Table I or Table Ib);

one or more of tetra-, hexa-, octa- and deca- (as referenced in Table Ia or Table Ib).

one or more of hexa-, octa-, deca-, and dodeca- (as referenced in Table Ia or Table Ib).

In a preferred embodiment the sample is evaluated for the amount of each of the size fractions in Table Ia or table Ib.

In a preferred embodiment, one or more structures from a subset of the size fractions in Table Ia or Table Ib are evaluated, e.g.:

one or more of structures tetra- and hexa- (as referenced in Table Ia or Table Ib);

one or more of structures tetra-, hexa- and octa- (as referenced in Table Ia or Table Ib);

one or more of structures hexa- and octa- (as referenced in Table Ia or Table Ib);

one or more of tetra-, hexa-, octa- and deca- (as referenced in Table Ia or Table Ib).

one or more of hexa-, octa-, deca-, and dodeca- (as referenced in Table Ia or Table Ib).

In one embodiment, the method further includes classifying, selecting, accepting or discarding, releasing or withholding, processing into drug product, shipping, moving to a different location, formulating, labeling, packaging, releasing into commerce, selling or offering to sell the preparation based, e.g., on the result of the determination or upon comparison to a reference standard.

In a preferred embodiment, the sample is evaluated with HPLC, e.g., HPLC is performed on one or more size fraction from an undigested LMWH preparation, e.g., an undigested enoxaparin preparation. In one embodiment the method includes: providing a proportioned LMWH preparation, e.g., a proportioned enoxaparin preparation; and subjecting a proportion of LMWH preparation to analysis, e.g., with HPLC, e.g., anion exchange HPLC such as strong anion exchange HPLC (SAX-HPLC), dynamic coated strong anion exchange HPLC and optionally, evaluating the presence, distribution, or amount, of a selected subject entity, e.g., a structure or species, e.g., a selected chain in a sample.

In a preferred embodiment, a saccharide structure and/or chain is evaluated using HPLC, e.g., anion exchange HPLC, e.g., carried out in a mobile phase under one or more of the following conditions: a mobile phase which is transparent to UV light with wavelengths of about 200 nm to about 400 nm; a mobile phase that comprises at least one salt chosen from sodium chloride, sodium acetate, potassium chloride, potassium acetate, potassium phosphate, ammonium phosphate, ammonium acetate, sodium phosphate monobasic, magnesium chloride, tris chloride, tris acetate, sodium perchlorate-sodium phosphate monobasic, methane sulfonic acid-ammonium methanesulfonate. In one embodiment, the chromatography is anion exchange chromatography such as strong anion exchange chromatography (SAX) e.g., using a Spherisorb™ SAX column, a Dionex CarboPac PA1, a Dionex CarboPac PA200, or Thermo Hypersil $C_8$ or $C_{18}$ e.g., wherein the strong anion exchange chromatography is carried out at a pH of about 2.0 to 9.0, e.g., about 2.5, about 3.5 or about 7.0.

In one embodiment, the chromatography is cetyltrimethyl ammonium HPLC (CTA-HPLC), e.g., using an octyl ($C_8$) to octadecyl ($C_{18}$) bonded silica coated with CTA, e.g., wherein the chromatography is carried out at a pH of about 1.0 to 5.0, e.g., about 2.5.

In one embodiment, prior to HPLC, the preparation, e.g., the enoxaparin preparation is proportioned and a portion of the preparation is subjected to analysis with HPLC. The preparation can be proportioned by a method which separates on the basis of one or more of size, charge or other physical or chemical properties. In one embodiment, the LMWH preparation, e.g., the enoxaparin preparation, is size fractionated, e.g., the method includes size fractionation of the preparation. The preparation can be fractionated using, e.g., one or more of FPLC, size exclusion chromatography GPC-HPLC (e.g., gel filtration chromatography), GPC-MS, dialysis and size exclusion filtration (e.g., ultrafiltration). The method can further include analyzing one or more fractions of the fractionated preparation to determine the presence of one or more specie or species, e.g., one or more chains of a trisaccharide, tetrasaccharide, hexasaccharide, octasaccharide, decasaccharide, dodecasaccharide or tetradecasaccharide fraction. In one embodiment, the method includes identifying the presence or absence of one or more chains from the fraction, e.g., as compared to a reference standard, e.g., a reference standard enoxaparin drug substance and/or enoxaparin drug product. In one embodiment, the method includes determining the sequence of one or more chains in a fraction. In another embodiment, the method can include determining the amount or the size distribution of one or more chains from the fraction. In one embodiment, the chain, e.g., the tetrasaccharide, hexasaccharide, octasaccharide, decasaccharide, dodecasaccharide chain, can be naturally associated with a starting material, e.g., UFH. In one embodiment, the chain can be an α or β anomer. In one embodiment, the chain (e.g., the tetrasaccharide, hexasaccharide, octasaccharide, decasaccharide, dodecasaccharide chain) can include a structural moiety not naturally associated with a starting material, e.g., UFH. For example, the structure not naturally associated with the starting material (also referred to herein as a "modified structural moiety") can be, e.g., a structure resulting from a method used to make the LMWH sample. In one embodiment, the preparation is an enoxaparin preparation and chain can include a modified structural moiety, e.g., one or more of: an mannosamine, an epoxide, a galacturonic acid, a $\Delta^{4,5}$ double bond at the non-reducing end, a 1,6 anhydro at the reducing end, or odd-number chain length (hexosamine at the reducing end).

In one embodiment, a tetrasaccharide fraction from the LMWH preparation, e.g., enoxaparin preparation, includes one or more of the following compounds:

TABLE II

| Peak # | Assignment |
|---|---|
| 1 | $\Delta UH_{NS6S}I_{2S}H_{NS6S}$ |
| 2 | $\Delta UH_{NS6S}I_{2S}H_{NS6S}$ |
|  | $\Delta U_{gal}H_{NS6S}I_{2S}Man_{NS6S}$ |
| 3 | $\Delta U_{2S}H_{NS6S}I_{2S}H_{NS}$ (α) |
| 4 | $\Delta U_{2S}H_{NS6S}I_{2S}H_{NS}$ (β), |
|  | $\Delta U_{2S}H_{NS6S}I_{2S}Man_{NS}$ (β) |
| 5 | $\Delta U_{2S}H_{NS6S}I_{2S}Man_{NS}$ (α), |
|  | $\Delta U_{2S}H_{NS}I_{2S}H_{NS6S}$ (α) |
| 6 | $\Delta U_{2S}H_{NS}I_{2S}H_{NS6S}$ (β) |
| 7 | $\Delta U_{2S}H_{NS6S}I_{2S}Man_{NS}$ (1,6 anhydro) |
| 8 | $\Delta U_{2S}H_{NS6S}I_{2S}H_{NS}$ (1,6 anhydro) |
| 9 | $\Delta U_{2S}H_{NS6S}G_{2S}H_{NS}$ (α) |
| 10 | $\Delta U_{2S}H_{NS6S}GH_{NS6S}$ (α) |
| 11 | $\Delta U_{2S}H_{NS6S}GMan_{NS6S}$ (α, β) |
| 12 | $\Delta U_{2S}H_{NS6S}I_{2S}H_{NS6S}$ (α), |
|  | $\Delta U_{2S}H_{NS6S}I_{2S}Man_{NS6S}$ (β) |
| 13 | $\Delta U_{2S}H_{NS6S}I_{2S}H_{NS6S}$ (β), |
|  | $\Delta U_{2S}H_{NS6S}I_{2S}Man_{NS6S}$ (α) |
| 14 | $\Delta U_{2S}H_{NS6S}G_{2S}H_{NS6S}$ (α) |
| 15 | $\Delta U_{2S}H_{NS6S}G_{2S}H_{NS6S}$ (β) |

Peaks identified in this Table correspond to those peaks identified in FIG. 1.

In one embodiment, a hexasaccharide fraction from the LMWH preparation, e.g., enoxaparin preparation, includes one or more of the following compounds:

TABLE III

| Hexa ID | Assignment |
|---|---|
| A | $\Delta U_{2S}H_{NS6S}I_{2S}H_{NS6S}GH_{NS6S}$ |
| B | $\Delta U_{2S}H_{NS6S}I_{2S}H_{NS6S}I_{2S}$ (60-65%) |
|   | $\Delta U_{2S}H_{NS6S}I_{2S}H_{NS6S}GH_{NS6S}$ (35-40%) |
| C | $\Delta U_{2S}H_{NS6S}I_{2S}H_{NS6S}I_{2S}H_{NS}(1,6)$ (56%) |
|   | $\Delta U_{2S}H_{NS6S}I_{2S}H_{NS6S}I_{2S}Man_{NS}(1,6)$ (44%) |
| D | $\Delta U_{2S}H_{NS6S}I_{2S}H_{NS6S}I_{2S}H_{NS6S}$ |
| E | $\Delta U_{2S}H_{NS6S}I_{2S}H_{NS6S}I_{2S}Man_{NS6S}$ |

In one embodiment, a octasaccharide fraction from the LMWH preparation, e.g., enoxaparin preparation, includes one or more of the following compounds:

TABLE IV

| Octa ID | Assignment | Relative Abundance |
|---|---|---|
| A | $\Delta U_{2S}H_{NS,6S}I_{2S}H_{NS}GH_{N4c}$-LR | 0.4% |
| B | $\Delta U_{2S}H_{NS,6S}I_{2S}H_{NS,6S}I_{2S}H_{NS,6S}GH_{NS}(1,6)$ (30%) | 0.7% |
|   | $\Delta U_{2S}H_{NS,6S}I_{2S}H_{NS,6S}I_{2S}H_{NS,6S}GMan_{NS}(1,6)$ (39%) | 0.9% |
|   | $\Delta U_{2S}H_{NS,6S}I_{2S}H_{NS,6S}I_{2S}H_{NS,6S}GH_{NS,6S}$ (31%) | 0.7% |
| C | $\Delta U_{2S}H_{NS,6S}I_{2S}H_{NS}I_{2S}H_{NS,6S}I_{2S}H_{NS,6S}$ | 1.6% |
| D | $\Delta U_{2S}H_{NS,6S}I_{2S}H_{NS,6S}I_{2S}H_{NS,6S}I_{2S}Man_{NS}(1,6)$ (80%) | 2.4% |
|   | $\Delta U_{2S}H_{NS,6S}I_{2S}H_{NS,6S}I_{2S}H_{NS,6S}I_{2S}H_{NS}(1,6)$ (20%) | 0.6% |
| E | $\Delta U_{2S}H_{NS,6S}I_{2S}H_{NS,6S}I_{2S}H_{NS,6S}GH_{NS,6S}$ | 5.1% |
| F | $\Delta U_{2S}H_{NS,6S}I_{2S}H_{NS,6S}I_{2S}H_{NS,6S}I_{2S}H_{NS,6S}$ (58%) | 3.6% |
|   | $\Delta U_{2S}H_{NS,6S}I_{2S}H_{NS,6S}I_{2S}H_{NS,6S}I_{2S}Man_{NS,6S}$ (42%) | 2.6% |
| G | $\Delta U_{2S}H_{NS,6S}GH_{NS,6S}I_{2S}H_{NS,6S}I_{2S}H_{NS,6S}$ | 2.6% |

Where LR = linkage region

The peaks identified in Table II and IV are derived from SAX-HPLC, the peaks identified in Table III are derived from CTA-SAX-HPLC. The structures are also determined using SAX-HPLC, and, when necessary, by other analytical methods, e.g., using CE on a sample digested with heparinase I, II and III, 2-O sulfatase and $\Delta^{4,5}$ glycuronidase, MALDI-MS and NMR. The combination of data allows determination of the structures of Table II, Table III and Table IV.

In a preferred embodiment, the method includes evaluating a subject entity to determine the amount of the subject entity in the sample. The amount can be evaluated in any way, e.g., in absolute terms, e.g., milligrams, or the level of the subject entity can be related to one or more or all of the other species in the sample. The amount can be expressed, e.g., in terms of % area under the curve (AUC), % chains, weight % or mole %.

In some embodiments, the amount of subject entity from a tetrasaccharide fraction is determined and then evaluated to determine if it is present in a preselected amount or range, e.g., an amount or range described herein, e.g., in Table V. This can be done by comparing with a range of reference values for the subject entity. E.g., an amount of one or all of the structures/chains evaluated, e.g., for presence or to determine if the subject entity is present in a range indicated in Table V.

In one embodiment, a percentage of one or more tetrasaccharide chains present in an undigested LMWH preparation, e.g., an enoxaparin preparation, has been determined, e.g., by % AUC, and preferably, the method includes determining or confirming that the percent of that tetrasaccharide chain is one or more of the following:

TABLE V

| | (Ranges are in Area %) | | | | | |
|---|---|---|---|---|---|---|
| Chain Sequencing Distribution by Area % | Range A Area % | | Range B Area % | | Range C Area % | |
| Peak 1 | 0.1 | 0.6 | Present or Detectable | | Present or Detectable | |
| Peak 2 | 0.6 | 1.2 | 0.6 | 1.2 | 0.4 | 1.4 |
| Peak 3 | 0.6 | 1.2 | 0.4 | 1.0 | 0.2 | 1.2 |
| Peak 4 | 1.8 | 3.6 | 1.7 | 4.1 | 0.9 | 4.9 |
| Peak 5 | 2.1 | 3.7 | 2.2 | 4.0 | 1.6 | 4.6 |
| Peak 6 | 0.5 | 1.6 | 0.4 | 1.6 | 0.0 | 2.0 |
| Peak 7 | 5.9 | 9.0 | 5.6 | 9.2 | 4.4 | 10.4 |
| Peak 8 | 7.0 | 9.9 | 6.6 | 10.2 | 5.4 | 11.4 |
| Peak 9 | 0.9 | 1.6 | 0.8 | 1.4 | 0.6 | 1.6 |
| Peak 10 | 5.0 | 6.2 | 4.9 | 6.7 | 4.3 | 7.3 |
| Peak 11 | 1.2 | 1.9 | 1.0 | 2.2 | 0.6 | 2.6 |
| Peak 12 | 39.7 | 48.0 | 38.1 | 48.9 | 34.5 | 52.5 |
| Peak 13 | 18.1 | 20.7 | 17.8 | 20.8 | 16.8 | 21.8 |
| Peak 14 | 2.3 | 4.0 | 1.9 | 4.3 | 1.1 | 5.1 |
| Peak 15 | 0.6 | 1.4 | 0.4 | 1.6 | 0.0 | 2.0 |

*Peaks referenced in this Table refer to the structures identified for these peak numbers in Table II.

In a preferred embodiment, the method includes providing a comparison of the value determined for a parameter with a reference value or values, to thereby evaluate the sample. In preferred embodiments, the comparison includes determining if the test value has a preselected relationship with the reference value, e.g., determining if it meets the reference value. The value need not be a numerical value but, e.g., can be merely an indication of whether the subject entity is present.

In a preferred embodiment the method includes determining if a test value is equal to or greater than a reference value, if it is less than or equal to a reference value, or if it falls within a range (either inclusive or exclusive of one or both endpoints). By way of example, the amount of a structure listed in Table V can be determined and, optionally shown to fall within a preselected range, e.g., a range which corresponds to a range A, B, C from Table V.

In one embodiment, the method further includes determining the presence, distribution and/or quantity of at least two or more (e.g., 1, 2, 3, 4, 5, 6, 7, 8, 9, 10, 11, 12, 13, 14, or 15) of the tetrasaccharide chains, e.g., the tetrasaccharide chains of Table II, in the preparation.

In a preferred embodiment, the sample is evaluated for the presence of each of the tetrasaccharide chains in Table II.

In a preferred embodiment, one or more structures from a subset of the tetrasaccharide chains in Table II are evaluated, e.g.:

one or more of the structures of peak 1, 2, 3, 4, 5, 6, 9, 11 and 15 (as referenced in Table II);

one or more of the structures of peak 7, 8, 10, 12, 13, and 14 (as referenced in Table II);

one or more of the structures of peak 7 and 8 (as referenced in Table II);

one or more of the structures of peak 4, 5, 7, 12 and 13 (as referenced in Table II).

In a preferred embodiment the sample is evaluated for the amount of each of the tetrasaccharide chains in Table V.

In a preferred embodiment, one or more structures from a subset of the tetrasaccharide chains in Table V are evaluated, e.g.:

One or more of the structures of peaks 1, 2, 3, 4, 5, 6, 9, 11 and 15 (as referenced in Table V);

one or more of the structures of peak 7, 8, 10, 12, 13, and 14 (as referenced in Table V);

one or more of the structures of peak 7 and 8 (as referenced-d in Table V);

one or more of the structures of peak 4, 5, 7, 12 and 13 (as references in Table V).

In one embodiment, the method further includes classifying, selecting, accepting or discarding, releasing or withholding, processing into drug product, shipping, moving to a different location, formulating, labeling, packaging, releasing into commerce, selling or offering to sell the preparation based, e.g., on the result of the determination or upon comparison to a reference standard.

In one aspect, the invention features a method of evaluating or processing a LMWH preparation e.g., enoxaparin, preparation, that includes making a determination about a LMWH, e.g., enoxaparin, preparation, based upon a method or analysis described herein. In one embodiment, the method further includes classifying, selecting, accepting or discarding, releasing or withholding, processing into drug product, shipping, moving to a different location, formulating, labeling, packaging, releasing into commerce, selling or offering to sell the preparation based, e.g., on the analysis. Thus, in a preferred embodiment the party making the evaluation does not practice the method or analysis described herein but merely relies on results which are obtained by a method or analysis described herein.

In one aspect, the invention features an enriched, isolated or purified preparation of a compound from Table II, Table III, or Table IV.

In one aspect, the invention features a set of standard preparations. The set includes a plurality of standards each having a different concentration of a compound of Table II, Table III or Table IV. Preferably the standard preparation is free of other carbohydrates. By way of example concentration can be evaluated in terms of weight/weight, weight/volume, or molarity. In a preferred embodiment the compound is provided in a solvent. The set of standards can be used in the evaluation of one or more sample, e.g., one can assay for a subject entity and compare the assay result with a value obtained from one or more of the standards. By way of example, one can determine he absorbance or other parameter and compare that with a standard curve for the relevant parameter derived from he set of standard preparations and determine the concentration of the subject entity.

In a preferred embodiment one or each standard in a set is, individually, an enriched, isolated, or purified preparation.

In a preferred embodiment the set includes at least 2, 3, 4, 5, or 10 standard preparations.

In another aspect, the invention features making a preparation, e.g., a standard preparation of known concentration, by providing a compound described herein and combining it with a solvent. In a preferred embodiment the standard is at least 70, 80, 90, 95, 99, 99.5, or 99.9% of the carbohydrate in the sample. The percentage can be determined by dry weight, chain, or molarity.

In one aspect, the invention features an isolated, enriched or purified tetrasaccharide fraction of an undigested enoxaparin sample.

In another aspect, the invention features an isolated, enriched or purified hexasaccharide fraction of an undigested enoxaparin sample.

In another aspect, the invention features an isolated, enriched or purified octasaccharide fraction of an undigested enoxaparin sample.

In another aspect, the invention features an isolated, enriched or purified size fraction of Table Ia or Table Ib.

Methods described herein can be used to evaluate a LMWH preparation by evaluating one or more subject entities revealed by FPLC, present in Table Ia or Table Ib or shown in FIG. 2, and/or by evaluating one or more subject entities revealed by HPLC or present in Table II, Table III or Table IV, e.g., in an amount present in Table V. Thus, methods described herein can be combined to provide analysis of a LMWH, e.g., enoxaparin.

Accordingly, in one aspect, the invention provides, a method of evaluating or processing a polysaccharide mixture, e.g., a LMWH, e.g., an enoxaparin preparation.

The method includes:

providing an evaluation of a parameter related to a subject entity from Table Ia or Table Ib or FIG. 2 or resolved by FPLC;

providing an evaluation of a parameter related to a subject entity from Table II, Table III, Table IV, Table V or resolved by HPLC;

and, optionally, providing a determination of whether a value (e.g., a value correlated to presence or absence, distribution, profile or amount) determined for the parameter for one or both the FIG. 2, Table Ia or Table Ib subject entity and the Table II, Table III, Table IV or Table V subject entity each meets a preselected criterion for that subject entity, e.g., is present or is present with a certain distribution, profile, or amount, e.g., an amount provided in Table Ia or Table Ib (for FPLC) or Table V (for HPLC), thereby evaluating or processing the mixture.

In a preferred embodiment, the method includes providing a comparison of the value determined for a parameter with a reference value or values, to thereby evaluate the sample. In preferred embodiments, the comparison includes determining if the test value has a preselected relationship with the reference value, e.g., determining if it meets the reference value.

Combination methods can incorporate any of the features or steps described herein for other methods. E.g., in preferred embodiments, the test value, or an indication of whether the preselected criterion is met, can be memorialized, e.g., in a computer readable record. By further example, a combination method can include embodiments wherein a decision or step is taken, e.g., the sample is classified, selected, accepted or discarded, released or withheld, processed into a drug product, shipped, moved to a new location, formulated, labeled, packaged, released into commerce, or sold or offered for sale, depending on whether the preselected criterion is met. E.g., based on the result of the determination or whether one or more subject entities is present, or upon comparison to a reference standard, the batch from which the sample is taken can be processed, e.g., as just described.

In one embodiment, the method includes providing one or more determinations from "a"-"n" (described below) for one or more subject entities from Table Ia, Table Ib and FPLC and providing one or more determinations from "m"-"aa" (described below) for one or more subject entities from Table II, Table III, Table IV or Table V:

For Table Ia and Table Ib:

a) determining the presence, distribution and/or quantity of at least two or more (e.g., 2, 3, 4 or 5) of the size fractions, e.g., the size fractions of Table Ia or Table Ib;

b) evaluating the presence and/or quantity of each of the size fractions in Table Ia or Table Ib.

c) evaluating one or more size fractions from a subset of the size fractions in Table Ia or Table Ib;

d) evaluating the presence and/or quantity of one or more of structures tetra- and hexa- (as referenced in Table Ia or Table Ib);

e) evaluating the presence and/or quantity of one or more of structures tetra-, hexa- and octa- (as referenced in Table Ia or Table Ib);

f) evaluating the presence and/or quantity of one or more of structures hexa- and octa- (as referenced in Table Ia or Table Ib);

g) evaluating the presence and/or quantity of one or more of tetra-, hexa-, octa- and deca- (as referenced in Table Ia or Table Ib).

and for FIG. 2 and FPLC, generally, h) determining the identity, presence, and/or quantity of at least two or more of: a lower molecular weight contaminant fraction; a fraction of trisaccharides; a fraction of tetrasaccharides; a fraction of hexasaccharides; a fraction of octasaccharides; a fraction of decasaccharides; a fraction of dodecasaccharides; a fraction of tetradecasaccharides; and a high molecular weight contaminant fraction;

i) evaluating the sample to determine if one or more of a tetrasaccharides fraction, a decasaccharides fraction and a dodecasaccharides fraction is present at an intensity lower than one or more of a hexasaccharide fraction and an octasaccharide fraction;

j) evaluating the sample to determine if the tetrasaccharide fraction is present at a lower intensity than the hexasaccharide and octasaccharide fractions;

k) evaluating the sample to determine if the decasaccharide fraction is present at an intensity similar to or lower than the octasaccharide and or hexasaccharide fraction;

l) evaluating the sample to determine if the dodecasaccharide fraction is present at an intensity lower than the hexasaccharide and octasaccharide fraction;

m) evaluating the sample to determine if the tetrasaccharide and dodecasaccharide fractions are present at an intensity less than the hexasaccharide and octasaccharide fraction and/or the decasaccharide fraction is present at a similar or lower intensity than the hexasaccharide and octasaccharide fraction; and n) evaluating the sample to determine if it has a size fraction profile similar to or identical with FIG. 2;

and for Table II and Table V:

o) determining the presence, distribution and/or quantity of at least two or more (e.g., 2, 3, 4, 5, 6, 7, 8, 9, 10, 11, 12, 13, 14 or 15) of the tetrasaccharide chains, e.g., the tetrasaccharide chains of Table II or Table V;

p) evaluating the presence of each of the tetrasaccharide chains in Table II.

q) evaluating the presence of one or more tetrasaccharide chains from a subset of the chains in Table II;

r) evaluating the presence of one or more of the chains of peaks 1, 2, 3, 4, 5, 6, 9, 11 and 15 (as referenced in Table II);

s) evaluating the presence of one or more of the chains of peaks 7, 8, 10, 12, 13, and 14 (as referenced in Table II);

t) evaluating the presence of one or more of chains of peaks 7 and 8 (as referenced in Table II);

u) evaluating sample for the presence of one or more of the chains of peaks 4, 5, 7, 12 and 13 (as referenced in Table II);

v) evaluating the sample for the amount of each of the tetrasaccharide chains in Table V;

w) evaluating the sample for the amount of one or more tetrasaccharide chains from a subset of the chains in Table V;

x) evaluating the sample for the amount of one or more of the tetrasaccharide chains of peaks 1, 2, 3, 4, 5, 6, 9, 11 and 15 in Table V;

y) evaluating the sample for the amount of one or more of the tetrasaccharide chains of peaks 7, 8, 10, 12, 13, and 14 in Table V;

z) evaluating the sample for the amount of one or more of the tetrasaccharide chains of peaks 7 and 8 in Table V;

aa) evaluating the sample for the amount of one or more of the tetrasaccharide chains of peaks 4, 5, 7, 12 and 13 in Table V.

In a preferred embodiment, determinations "a" and "o" are made.

In a preferred embodiment, determinations "a" and "p" are made.

In a preferred embodiment, determinations "a" and "q" are made.

In a preferred embodiment, determinations "a" and "r" are made.

In a preferred embodiment, determinations "a" and "s" are made.

In a preferred embodiment, determinations "a" and "t" are made.

In a preferred embodiment, determinations "a" and "u" are made.

In a preferred embodiment, determinations "a" and "v" are made.

In a preferred embodiment, determinations "a" and "w" are made.

In a preferred embodiment, determinations "a" and "x" are made.

In a preferred embodiment, determinations "a" and "y" are made.

In a preferred embodiment, determinations "a" and "z" are made.

In a preferred embodiment, determinations "a" and "aa" are made.

In a preferred embodiment, determination "b" and "v" are made.

In a preferred embodiment, determination "b" and "w" are made.

In a preferred embodiment, determination "b" and "x" are made.

In a preferred embodiment, determination of "b" and "y" are made.

In a preferred embodiment, determination of "b" and "z" are made.

In a preferred embodiment, determination of "b" and "aa" are made.

In a preferred embodiment, determination of "d" and "p" are made.

In one aspect, the invention features a method of analyzing a process, e.g., manufacturing process, of a LMWH, e.g., an enoxaparin, e.g., an enoxaparin made by a selected process. The method includes: providing a LMWH, e.g., enoxaparin, preparation; analyzing the LMWH, e.g., enoxaparin, preparation using, e.g., a method described herein, e.g., to identify and/or quantify one or more structure and/or chain, e.g., one or more structure and/or chain disclosed herein, thereby allowing analysis, e.g., qualitative and/or quantitative analysis, of the one or more structure and/or chain in the LMWH, e.g., enoxaparin, preparation. In one embodiment, the method further includes comparing the size distribution, profile or amount of the one or more structural and/or chain with a reference value, to thereby analyze the manufacturing process.

In one embodiment, the method further includes maintaining the manufacturing process based, at least in part, upon the analysis. In one embodiment, the method further includes altering the manufacturing process based, at least in part, upon the analysis.

In one aspect, the invention features a method of analyzing a process, e.g., a manufacturing process. The method includes: providing a LMWH, e.g., enoxaparin, preparation manufactured by a process that includes treatment with sodium hydroxide and heat; analyzing the LMWH, e.g., enoxaparin, preparation using, e.g., a method described herein, to identify one or more (e.g., one, two, three, four, five, six, seven, eight, nine, ten, eleven, twelve, thirteen, fourteen, fifteen) tetrasaccharides in an enoxaparin preparation to thereby allowing analysis of the enoxaparin preparation; and optionally, comparing to a reference value, to thereby analyze the manufacturing process. In one embodiment, the tetrasaccharide is one or more of the tetrasaccharides provided in Table II or Table V. The absence or presence of a tetrasaccharide or tetrasaccharides can indicate whether the sodium hydroxide and heat step of manufacture needs to be modified.

In one embodiment, the method further includes maintaining the manufacturing process based, at least in part, upon the analysis. In one embodiment, the method further includes altering the manufacturing process based, at least in part, upon the analysis.

In a preferred embodiment, the method includes evaluating a process, e.g., manufacturing process, of a LMWH, e.g., an enoxaparin, e.g., an enoxaparin made by a selected process, that includes making a determination about the process, e.g., manufacturing process, or LMWH, e.g., enoxaparin, e.g., enoxaparin made by a selected process, based upon a method or analysis described herein. In one embodiment, the method further includes maintaining or altering the manufacturing process based, at least in part, upon the method or analysis. Thus, in a preferred embodiment the party making the evaluation does not practice the method or analysis described herein but merely relies on results which are obtained by a method or analysis described herein.

In a preferred embodiment, the method includes comparing two or more heparin preparations, e.g., LMWH preparations, e.g., two or more enoxaparin preparations, e.g., in a method of monitoring or controlling batch-to-batch variation or to compare a preparation to a reference standard. This embodiment includes: providing a first heparin preparation; providing the presence, amount, profile or size distribution of one or more structure, chain or fraction, e.g., one or more structure, chain or fraction described herein, in the first sample; optionally, providing a second heparin preparation; providing the presence, size distribution, profile or amount of a structure, chain or fraction in the second preparation; and comparing the presence, size distribution, profile or amount of the one or more structure, chain or fraction of the first heparin preparation with the one or more structure, chain or fraction of the second heparin preparation. In one embodiment, the one or more structure, chain or fraction is analyzed by a method described herein.

In one embodiment, the method can further include making a decision, e.g., to classify, select, accept or discard, release or withhold, process into drug product, move to a different location, ship, formulate, label, package, release into commerce, sell or offer to sell the preparation, based, at least in part, upon the determination, and optionally, carrying out the decision.

In one aspect, the invention features a method of making a batch of enoxaparin having a preselected property, e.g., meeting a release specification, label requirement, or compendial requirement, e.g., a property described herein. The method includes:
  providing a test enoxaparin preparation;
  analyzing the test enoxaparin preparation according to a method described herein;
  determining if the test enoxaparin preparation includes the presence distribution or amount of a structure or species of Table II, Table III, Table IV or Table V or includes the presence, distribution, profile or amount of one or more of the size fractions of Table Ia, Table Ib or shown in FIG. 2, and selecting the test enoxaparin preparation to make enoxaparin, thereby making a batch of enoxaparin.

In one aspect, the invention features a method of predicting or ensuring that a batch of enoxaparin will have a preselected property, e.g., that it will meet a release specification, label requirement, or compendial requirement, e.g., a property described herein. The method includes:
  providing a test enoxaparin preparation;
  analyzing the test enoxaparin preparation according to a method described herein;
  wherein satisfaction of the preselected reference, e.g., one or more reference disclosed herein, by the test enoxaparin preparation, is predictive of or ensures that a batch of enoxaparin made from the test enoxaparin preparation will have a preselected property, e.g., it will meet a release specification, label requirement, or compendial requirement, e.g., a property described herein.

In one aspect, the invention features a method of making one or more batches of a polysaccharide preparation, e.g., an enoxaparin preparation, wherein one or more glycoprofile values (e.g., one or more structural property, e.g., the presence, size distribution, profile or quantity of a structure, chain or fraction described herein) of the batches varies less than a preselected range or has some preselected relationship with a reference standard. For example, it is present at a lower, higher, or equivalent level as a standard or is within (or outside) a range of values. Preferably, evaluation of the value, e.g., the presence of a structure, chain or size fraction, is made by a method described herein. In some embodiments, the method further includes classifying or selecting one or more batches having a structural property that varies less than the preselected range, e.g., a range described herein.

In another aspect, the invention features multiple batches of a polysaccharide preparation, e.g., an unfractionated heparin preparation or enoxaparin preparation, wherein one or more glycoprofile values (e.g., a value determined by a method described herein, for each batch varies less than a preselected range from a pre-selected desired glycoprofile, e.g., a range described herein for enoxaparin. In some embodiments, the method includes determining one or more subject entity (e.g., one or more structure, chain or fraction) of one or more batches of a product, and selecting a batch as a result of the determination. In some embodiments, the method can also include comparing the results of the determination to preselected values, e.g., a reference standard. In other embodiments, the method can further include adjusting the dose of the batch to be administered, e.g., based on the result of the determination of the subject entity. Preferably, evaluation of the value, e.g., the presence of one or more structure, chain or fraction, is made by a method described herein.

In another aspect, the invention features a method of determining a reference value for a polysaccharide composition, e.g., an enoxaparin preparation, and determining the presence and/or amount of one or more structure, chain or fraction described herein including those provided in Table II, III, IV, and V and/or determining the presence, size distribution or profile of one or more fraction provided in Table Ia, Table Ib and described herein including those shown in FIG. 2. Preferably, evaluation of the value, e.g., the presence, size distribution, or quantity of the one or more structure, chain or fraction, is made by a method described herein.

In another aspect, the invention features a method for determining bioequivalence. The method includes some or all of the following: providing or determining a value for the presence, amount, profile or size distribution of one or more structure, chain or fraction, e.g., one or more structure, chain or fraction described herein, in a first heparin preparation, e.g. an enoxaparin preparation; providing or determining the bioavailability of the preparation; providing a reference value, e.g., by providing or determining presence, amount, profile or size distribution of one or more structure, chain or fraction, e.g., one or more structure, chain or fraction described herein, in a second heparin preparation, e.g., an enoxaparin preparation, and comparing the presence, amount, profile or size distribution of one or more structure, chain or fraction of the first preparation and/or the reference value, e.g., a second heparin preparation. Preferably, evaluation of the one or more structure chain, or fraction is made by a method described herein.

In some embodiments, the method further comprises monitoring for presence, tissue distribution, spatial distribution, temporal distribution or retention time, in a cell or a subject, e.g., an experimental animal. In some embodiments, the method includes determining the presence, amount, profile or size distribution of one or more structure, chain or fraction described herein of one or more batches of a product. In some embodiments, the method further includes selecting a batch as a result of the determination. In some embodiments, the method further includes comparing the results of the determination to preselected values, e.g., a reference standard.

In another aspect, the invention provides a method for determining the safety or suitability of a heparin, e.g., a LMWH, preferably an enoxaparin preparation for use in a particular indication. The method includes some or all, typically all, of the following: determining the presence, amount, profile or size distribution of one or more structure, chain or fraction, e.g., one or more structure, chain or fraction described herein, in the heparin; providing a reference value or sample; determining if the heparin is acceptable, e.g., by comparing a value for the presence, amount, profile or size distribution of one or more structure, chain or fraction of the heparin with the reference value or with a value determined from the sample. For example, when the heparin is enoxaparin, one or more of the structures, chains or fractions described herein can be used as a reference. When a preselected index of similarity is met, the heparin can be determined to be safe or suitable. In some embodiments, the reference sample is associated with one or more undesired effects. In some embodiments, the reference sample is associated with one or more desired effects. Preferably, evaluation of the presence, amount, profile or size distribution of the one or more structure, chain or fraction, e.g., one or more structure, chain or fraction described herein, in the heparin is made by a method described herein.

In another aspect, the invention features a method of one or more of providing: a report to a report receiving entity; evaluating a sample of enoxaparin for compliance with a reference standard, e.g., an FDA requirement; seeking indication from another party that an enoxaparin sample meets some predefined requirement; or submitting information about an enoxaparin sample to another party. Exemplary receiving entities or other parties include a government, e.g., the U.S. federal government, e.g., a government agency, e.g., the FDA.

The method includes one or more (and preferably all) of the following:

performing one or more steps in making and/or testing a batch of enoxaparin in a first country, preferably the United States;

sending at least an aliquot of the sample outside the first country, e.g., sending it outside the United States, to a second country;

preparing, or receiving, a report which includes data about the structure of the enoxaparin sample, e.g., data related to a structure, chain or fraction described herein, e.g., data generated by one or more of the methods described herein;

providing said report to a report recipient entity.

In a preferred embodiment the report receiving entity can determine if a predetermined requirement or reference value is met by said data and optionally, a response from the report receiving entity is received, e.g., by a manufacturer, distributor or seller of enoxaparin. In a preferred embodiment, upon receipt of approval from said report recipient entity, enoxaparin from said batch is selected, packaged, or placed into commerce.

In one aspect, the invention features a method of evaluating a sample of enoxaparin that includes receiving data with regard to the presence or level of a structure, chain or fraction described herein in an enoxaparin sample, e.g., wherein the data was prepared by one or more methods described herein; providing a record which includes said data and optionally includes an identifier for a batch of enoxaparin; submitting said record to a decision-maker, e.g., a government agency, e.g., the FDA; optionally, receiving a communication from said decision maker; optionally, deciding whether to release market the batch of Lovenox or enoxaparin based on the communication from the decision maker. In one embodiment, the method further includes releasing the sample.

Any of the methods described herein can further include determining and/or providing an analysis regarding one or more biological activity of the preparation or sample. For example, the biological activity can be one or more of anti-Xa activity, anti-IIa activity, molecular weight distribution and average molecular weight. The methods can further include comparing any of anti-Xa activity, anti-IIa activity, molecular weight distribution and average molecular weight to a reference standard for enoxaparin. In one embodiment, the reference standard for anti-Xa activity is about 75 to 150 IU/mg, e.g., 100 IU/mg; the reference standard for anti-IIa activity is about 30 IU/mg; the reference standard for molecular weight distribution is 16% are <2000 Da species, greater than or equal to 68% are 2000-8000 Da species, and less than or equal to 18% are >8000 Da species; the reference standard for the average molecular weight is about 4300 to 4800 Da, e.g., 4500 Da. In one embodiment the reference standard is having 15% to 30%, e.g., 15% to 25% or 20% to 30% (e.g., 20% to 28%) chains terminating in a 1,6 anhydro structure, e.g., a measured by weight average molecular weight or total percentage of chains.

A "polysaccharide" as used herein is a polymer composed of monosaccharides linked to one another. In many polysaccharides, the basic building block of the polysaccharide is actually a disaccharide unit, which can be repeating or non-repeating. Thus, a unit when used with respect to a polysaccharide refers to a basic building block of a polysaccharide and can include a monomeric building block (monosaccharide) or a dimeric building block (disaccharide).

A polysaccharide according to the invention can be a mixed population of polysaccharides, e.g., a heparin preparation e.g., synthetic heparin preparation, an unfractionated heparin preparation or LMWH preparation. As used herein, a "mixed population of polysaccharides" is a polydisperse mixture of polysaccharides. The term "polydisperse" or "polydispersity" refers to the weight average molecular weight of a composition (Mw) divided by the number average molecular weight (Mn). The polydispersity of unfractionated heparin and various LMWHs are known, as are methods for determining polydispersity. Compositions with polydispersity near 1 are more homogeneous, containing fewer different polysaccharides. As an example, a preparation of unfractionated heparin, which contains a wide variety of polysaccharides of differing lengths and compositions, has a polydispersity of about 1.5 to 2.0.

The term "enoxaparin preparation" as used herein refers to both enoxaparin drug substance preparations and enoxaparin drug product preparations. The term "drug product preparation" refers to a polysaccharide preparation having the purity required for and being formulated for pharmaceutical use. The term "drug substance preparation" refers to a preparation having the polysaccharide constituents for pharmaceutical use but is not necessarily in its final formulation and/or comprises one or more non-product contaminant (e.g., one or more inorganic product such as sulfate, chloride, acetate and phosphates, protein contaminant, process by-product such as benzyl alcohol and benethonium).

The term "unfractionated heparin (UFH)" as used herein, is heparin purified from porcine intestinal mucosa that can be used as a starting material in the process to form enoxaparin.

The term "enriched preparation" as used herein is a preparation which is significantly enriched for the subject entity, e.g., a structure or chain. Significant enrichment can, by way of example, be based on weight/weight, chain number analysis or molarity. Enrichment can be with respect to a naturally occurring material, in UFH or in a LMWH, e.g., enoxaparin. In some embodiments, in the case of a subject entity which is present in UFH, the subject entity is present in the enriched preparation at least 2, 5, 10, 50 or 100 times the concentration (as determined, e.g., by weight/weight, chain number analysis or molarity) it is found in UFH. In some embodiments, in the case of a subject entity which is present in enoxaparin, the subject entity is present in the enriched preparation at least 2, 5, 10, 50 or 100 times the concentration (as determined, e.g., by weight/weight, chain number analysis or molarity) it is found in enoxaparin. In some embodiments the subject entity can be accompanied by a solvent, diluent, or carrier. In other embodiments the subject entity is substantially free of a solvent, diluent, or carrier. In some embodiments the subject entity can be accompanied by a medium, e.g., a buffer, matrix or other material used to effect separation and/or eluent, used in its purification. In other embodiments the preparation is substantially free of such elements. In a preferred embodiment the preparation is provided in an enclosure which is substantially free of contaminant carbohydrates.

The term "isolated preparation" as used herein refers to a preparation containing a subject entity, e.g., a structure or chain, that is substantially free of at least one and preferably all other carbohydrate with which it normally occurs. By way of example, in the case of a subject entity present in UFH the subject entity is substantially free of at least one and preferably all other carbohydrate (a contaminating carbohydrate) with which it occurs in UFH. In the case of a subject entity present in enoxaparin the subject entity is substantially free of at least one and preferably all other carbohydrate with which it occurs in enoxaparin. Substantially free means that least 70, 80, 90, 95, 99, 99.5 or 99.9%, or substantially all, of a contaminating entity, e.g., a carbohydrate, has been removed. This determination can, by way of example, be based on weight/weight or chain number analysis. In some embodiments the subject entity can be accompanied by a solvent, diluent, or carrier. In other embodiments the subject entity is substantially free of a solvent, diluent, or carrier. In some embodiments the subject entity can be accompanied by a medium, e.g., a buffer, matrix or other material used to effect separation and/or eluent, used in its purification. In other embodiments the preparation is substantially free of such elements. In a preferred embodiment the preparation is provided in an enclosure which is substantially free of contaminant carbohydrates. In some embodiments, in the case of a subject entity which is present in UFH, the subject entity is present in the isolated preparation at least 2, 5, 10, 50 or 100 times the concentration (as determined, e.g., by weight/weight, chain number analysis or molarity) it is found in UFH. In some embodiments, in the case of a subject entity which is present in enoxaparin, the subject entity is present in the isolated preparation at least 2, 5, 10, 50 or 100 times the concentration (as determined, e.g., by weight/weight, chain number analysis or molarity) it is found in enoxaparin.

The term "purified preparation" as used herein refers to a preparation containing a subject entity, e.g., a structure or chain, that is at least 70, 80, 90, 95, 99, 99.5 or 99.9% the subject entity or is substantially all subject entity. This determination can, by way of example, be based on weight/weight or chain number analysis. In some embodiments the subject entity can be accompanied by a solvent, diluent, or carrier. In some embodiments the subject entity can be accompanied by a medium, e.g., a buffer, matrix and/or eluent, used in its purification. In other embodiments the purified preparation does not contain a solvent, diluent, carrier or medium used in purification. In a preferred embodiment the purified preparation is provided in an enclosure which is substantially free of contaminant carbohydrates. In some embodiments, the case of a subject entity which is present in UFH, the subject entity is present in the purified preparation at least 2, 5, 10, 50 or 100 times the concentration (as determined, e.g., by weight/weight, chain number analysis or molarity) it is found in UFH. In some embodiments, in the case of a subject entity which is present in enoxaparin, the subject entity is present in the purified preparation at least 2, 5, 10, 50 or 100 times the concentration (as determined, e.g., by weight/weight, chain number analysis or molarity) it is found in enoxaparin.

The term "enriched size class preparation" or "enriched size fraction preparation" (wherein size class refers to a saccharide of a certain length, e.g., tetrasaccharide, octasaccharide, and the like) as used herein is a preparation which is significantly enriched for the subject size class, e.g., a tetrasaccharide. Significant enrichment can, by way of example, be based on weight/weight, chain number analysis or molarity. Enrichment can be with respect to a naturally occurring material, in UFH or in a LMWH, e.g., enoxaparin. In the case of a subject size class which is present in UFH, the subject size class is present in the enriched preparation at least 2, 5, 10, 50 or 100 times the concentration (as determined, e.g., by weight/weight, chain number analysis or molarity) it is found in UFH. In the case of a subject size class which is present in enoxaparin, the subject size class is present in the enriched preparation at least 2, 5, 10, 50 or 100 times the concentration (as determined, e.g., by weight/weight, chain number analysis or molarity) it is found in enoxaparin. In some embodiments the subject size class can be accompanied by a solvent, diluent, or carrier. In other embodiments the subject size class is substantially free of a solvent, diluent, or carrier. In some embodiments the subject size class can be accompanied by a medium, e.g., a buffer, matrix or other material used to effect separation and/or eluent, used in its purification. In other embodiments the preparation is substantially free of such elements. In a preferred embodiment the preparation is provided in an enclosure which is substantially free of contaminant carbohydrates.

The term "isolated size class preparation" or "isolated size fraction preparation" (wherein size class refers to a saccharide of a certain length, e.g., tetrasaccharide, octasaccharide, and the like) as used herein refers to a preparation containing saccharides of a selected size class that is substantially free of saccharides of at least one and preferably all other size classes. Substantially free means that least 70, 80, 90, 95, 99, 99.5 or 99.9%, or substantially all, of a contaminating carbohydrate size class have been removed. This determination can, by way of example, be based on weight/weight or chain number analysis. In some embodiments the subject size class saccharides can be accompanied by a solvent, diluent, or carrier. In some embodiments the subject size class saccharides can be accompanied by a medium, e.g., a buffer, matrix and/or eluent, used in its purification. In other embodiments the isolated preparation does not contain a solvent, diluent, carrier or medium used in purification. In a preferred embodiment the isolated preparation is provided in an enclosure which is free of contaminant size classes. In some embodiments, in the case of a subject size class saccharides which is present in UFH, the subject size class is present in the isolated preparation at least 2, 5, 10, 50 or 100 times the concentration (as determined, e.g., by weight/weight, chain number analysis or molarity) it is found in UFH. In some embodiments, in the case of a subject size class which is present in enoxaparin, the subject size class saccharides is present in the isolated preparation at least 2, 5, 10, 50 or 100 times the concentration (as determined, e.g., by weight/weight, chain number analysis or molarity) it is found in enoxaparin.

The term "purified size class preparation" or "purified size fraction preparation" (wherein size class refers to a saccharide of a certain length, e.g., tetrasaccharide, octasaccharide, and the like) as used herein refers to a preparation containing a subject size class, that is at least 70, 80, 90, 95, 99, 99.5 or 99.9% the subject size class or is substantially all subject size class. This determination can, by way of example, be based on weight/weight or chain number analysis. In some embodiments the subject size class can be accompanied by a solvent, diluent, or carrier. In some embodiments the subject size class can be accompanied by a medium, e.g., a buffer, matrix and/or eluent, used in its purification. In other embodiments the purified preparation does not contain a solvent, diluent, carrier or medium used in purification. In a preferred embodiment the purified preparation is provided in an enclosure which is substantially free of contaminant carbohydrates. In some embodiments, the case of a subject size class which is present in UFH, the subject size class is present in the purified preparation at least 2, 5, 10, 50 or 100 times the concentration (as determined, e.g., by weight/weight, chain number analysis or molarity) it is found in UFH. In some embodiments, in the case of a subject size class which is present in enoxaparin, the subject size class is present in the purified preparation at least 2, 5, 10, 50 or 100 times the concentration (as determined, e.g., by weight/weight, chain number analysis or molarity) it is found in enoxaparin.

Complex polysaccharide drug products can be isolated or derived from natural sources and are complex mixtures of polysaccharide chains that differ from one another both in terms of size and chemical sequence that comprises each polysaccharide chain. Chain sequence differences can arise both from differences intrinsic to the cell and tissue-specific biosynthesis pathway by which these complex polysaccharides are made as well as from differences that arise as a function of the process of isolating or preparing polysaccharide substances from natural sources. For example, the LMWHs are derived from unfractionated heparin (UFH) primarily through chemical or enzymatic depolymerization of the polysaccharide chains. Different LMWHs can be made by various depolymerization processes. A process used to make a LMWH can cause one or more unique structural modifications to the polysaccharide chains of the polysaccharide drug, such as heparin. For example, esterification of the carboxylate functional group on the uronic acid followed by β-elimination results in the formation of a $\Delta^{4,5}$ double bond on the non-reducing end as well as the formation of some chains having 1,6-anhydro derivatives. In addition, differences can arise in LMWH preparations due to variation in the starting material. As a result of these structural differences, different LMWHs can have distinct pharmacological and/or structural profiles.

The details of one or more embodiments of the invention are set forth in the accompanying drawings and the description below. Other features, objects, and advantages of the invention will be apparent from the description and drawings, and from the claims.

DETAILED DESCRIPTION

The drawings are first briefly described.

REFERENCE VALUES AND STANDARDS

Figure 1:
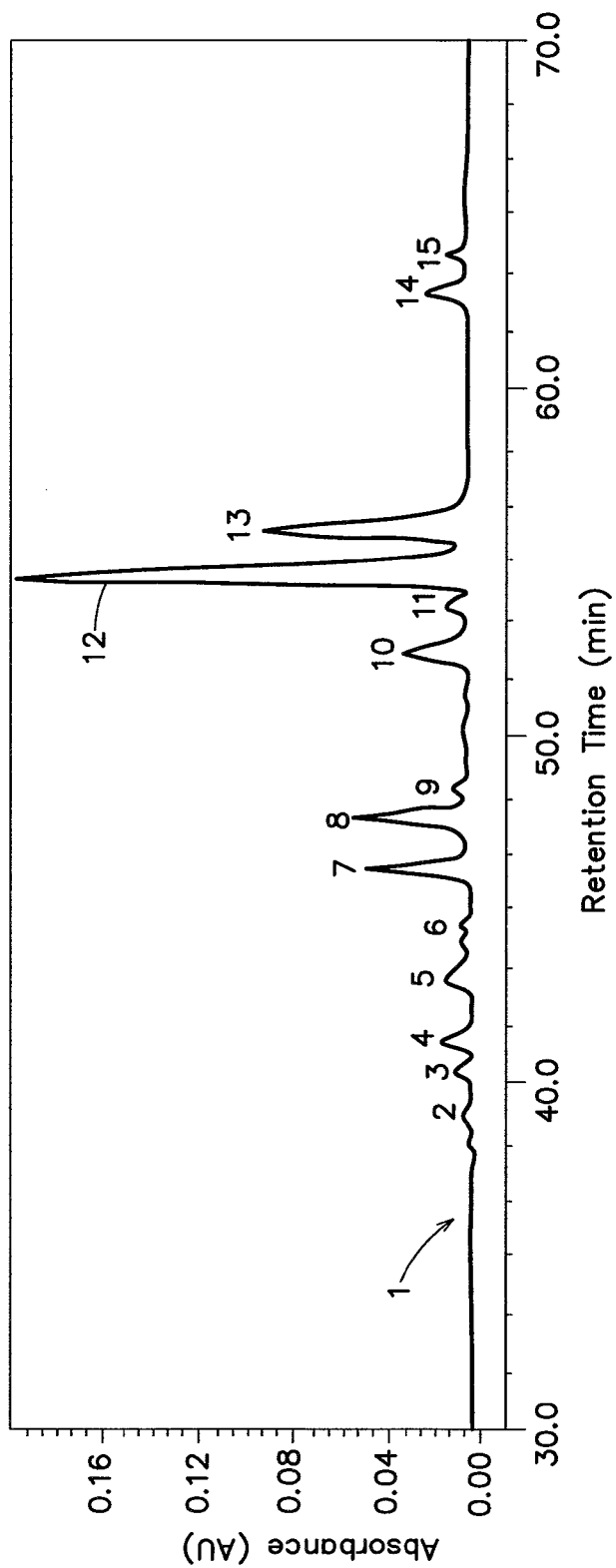
FIG. 1 is a trace of UV absorbance at 232 nm of a SAX-HPLC analysis of tetrasaccharide chains of an enoxaparin preparation. The peaks are identified in Table I.

A reference value, by way of example, can be a value determined from a reference sample (e.g., a commercially available sample or a sample from previous production). E.g., a reference value can be a value for the presence of a subject entity in a sample, e.g., a reference sample. The reference value can be numerical or non-numerical. E.g., it can be a qualitative value, e.g., yes or no, or present or not present at a preselected level of detection, or graphic or pictorial. The reference value can also be values for the presence of more than one subject entity in a sample. For example, the reference value can be a map of structures present in enoxaparin when analyzed by HPLC, e.g., an HPLC method described herein and/or when analyzed by FPLC, e.g., an FPLC method described herein. The reference value can also be a release standard (a release standard is a standard which should be met to allow commercial sale of a product) or production standard, e.g., a standard which is imposed, e.g., by a party, e.g., the FDA, on a LMWH, e.g., enoxaparin.

The reference standard can be derived from any of a number of sources. The reference standard can be one which was set or provided by (either solely or in conjunction with another party, e.g., a regulatory agency, e.g., the FDA) the manufacturer of the drug or practitioner of a process to make the drug. The reference standard can be one which was set or provided by (either solely or in conjunction with another party, e.g., a regulatory agency, e.g., the FDA) a party other than the party manufacturing a drug and practicing a method disclosed herein, e.g., another party which manufactures the drug or practices a process to make the drug. The reference standard can be one which was set or provided by (either solely or in conjunction with another party) a regulatory agency, e.g., the FDA, to the manufacturer of the drug or practitioner of the process to make the drug, or to another party licensed to market the drug. E.g., the reference standard can be a production, release, or product standard required by the FDA. In preferred embodiments, a reference standard is a standard required of a pioneer drug (e.g., a drug marketed under an approved NDA) or a generic drug (e.g., a drug marketed or submitted for approval under an ANDA).

The reference standard can be one which was set or provided by Aventis Pharma SA, its fully owned subsidiaries, its successors and assigns or agents, either solely or in conjunction with another party, e.g., a regulatory agency, e.g., the FDA, for production or release of a LMWH, e.g., enoxaparin.

The reference standard can be one which was set or provided by Momenta Pharmaceuticals, Inc., its fully owned subsidiaries, its successors and assigns or agents, either solely or in conjunction with another party, e.g., a regulatory agency, e.g., the FDA, for production or release of a LMWH, e.g., enoxaparin.

The reference value can be a statistical function, e.g., an average, of a number of values. The reference value can be a function of another value, e.g., of the presence or distribution of a second entity present in the sample, e.g., an internal standard.

Evaluation against a reference value can be used to determine if a particular structure or chain is present in an enoxaparin sample.

Treatment of Enoxaparin Preparation and Analysis Using FPLC

A sample described herein (e.g., a LMWH such as enoxaparin or Lovenox™) can be lyophilized and/or dried in a vacuum oven, e.g., at about 40° C., 43° C., 46° C., 49° C., 52° C. or 55° C., for about 2, 4, 6, 8, 10, 12, 14, 16, 18, 20, 22 or 24 hours. For example, the sample can be lyophilized and/or dried under one of the following conditions: 40° C. for 12 hours; 46° C. for 8 hours; 49° C. for 6 hours; 52° C. for 4 hours. A lyophilized o dried sample can be reconstituted in water or a suitable buffer at a concentration of about 1, 2, 5, 10, 15, 20, 50 mg/mL.

Various size fractions of the sample can be differentiated from each other using size exclusion chromatography with FPLC. Preferably about 50 to 150 mg of sample is loaded into a size exclusion resin. A size exclusion column can be selected by its potential fractionate LMWHs on the basis of molecular weight. For example, resins having a molecular weight range of about 100 to 30,000 Da, e.g., about 500 to 30,000 Da, about 500 to 20,000 Da, about 1,500 to 20,000 Da, about 100 to 10,000 Da, about 100 to 8,000 Da, about 100 to 7,000 Da. Examples of suitable resins include Superdex30™ (GE Healthcare), Toyopearl HW40™ (Tosoh), Toyopearl HW50™ (Tosoh) and P-10 Gel™ (Biorad).

The sample can be injected onto the column using a suitable running buffer such as one or more of sodium chloride, sodium phosphate, disodium hydrogen phosphate dodecahydrate and trisodium hydrogen phosphate dodecahydrate at a pH of about 5 to 9, e.g., 6 to 8. An exemplary running buffer is 5 mM $Na_2HPO_4$ and 150 mM NaCl at a pH of about 7.2. The run time can be about 2 to 10 hours, e.g., 4 to 8, e.g., 6 hours. Fractions are evaluated at 232 nm and can be plotted as absorbance versus volume (mL.)

The amount of each size fraction present can be determined, e.g., based upon the percent area under the curve.

Treatment of Enoxaparin Preparation and Chain Analysis by HPLC

As an alternative to analyzing complex polysaccharides as a whole, the sample, e.g., LMWH, e.g., enoxaparin, size separated into uniform fractions. One or more fractions can then be analyzed, e.g., using methods described herein. Size fractionations can be effected by a variety of methods e.g., size exclusion chromatography, FPLC, GPC-MS. For example, the sample can be size fractional using an FPLC method described herein. Size defined saccharides can be collected by a fraction collector, desalted and lyophilized to dryness.

Preferably about 15 to 50 µl of sample is loaded onto the column. Substrates, e.g., resins or beads, suitable for strong anion exchange HPLC include those with strongly basic (cationic) groups such as quaternary ammonium groups (e.g., quaternary amine groups), tertiary sulfonium groups, quaternary phosphonium groups, or alkyl pyridinium groups. The substrate can be, e.g., a cetyltrimethylammonium coated $C_8$ or $C_{18}$ substrate. The substrate can be of various particle sizes, including 3 µm, 5 µm, 10 µm. The particles can be nonporous. Preferably the resin or bead has one or more of the following properties: it has rapid mass transfer; a high pH stability; mechanical stability.

Useful mobile phases include a salt such as sodium chloride, sodium acetate, potassium chloride, potassium acetate, potassium phosphate, ammonium phosphate, ammonium acetate, sodium phosphate monobasic, magnesium chloride, tris chloride, tris acetate, sodium perchlorate-sodium phosphate monobasic, methane sulfonic acid-ammonium methanesulfonate. In some embodiments, the mobile phase uses a gradient of a salt. For example, the salt concentration can increase from, e.g., about 0.0, 0.1, 0.2, 0.3, 0.4, 0.5, 0.6, 0.7, or 0.8 M, to, e.g., about 1.5, 1.6, 1.7, 1.8, 1.9, 2.0, 2.1, 2.2, 2.3, 2.4, or 2.5 M, over a period of time, e.g., about 30, 45, 60, 75, 90, 105, 120, 135, 150, 165, 180, 195, or 210 minutes. The gradient can be either a linear or non-linear gradient. For example, the gradient can be multiphasic, e.g., biphasic, triphasic, etc. For example, a linear gradient of sodium chloride can increase from about 0.2M to 2M over 60 to 180, or 60 to 140 minutes. The flow rate for this example is preferably about 1.0 to 1.4 ml/minute. The mobile phase can be maintained at a constant or near-constant pH, e.g., a pH of about 2.0, 2.5, 3.0, 3.5, 4.0, 4.5, 5.0, 5.5, 6.0 or 6.5, 7.0.

The column can be maintained at a constant temperature throughout the separation, e.g., using a commercial column heater. In some embodiments, the column can be maintained at a temperature from about 18° C. to about 70° C., e.g., about 18° C., 20° C., 22° C., 25° C., 30° C., 37° C., 40° C., 45° C., 50° C., 55° C., 60° C., 65° C., or 70° C. In some embodiments, the column is at ambient temperature.

Species separated by the methods described herein can be detected by numerous means, e.g., by ultraviolet absorbance (e.g., at a wavelength of about 232 nm), evaporative light scattering, fluorescence, pulsed amperometric detection, and mass spectrometry. In some embodiments, two or more means of detection can be utilized on the same sample, e.g., in series or in parallel.

Additionally, an internal standard can be used in the methods described herein. When an internal standard is used, it can be separated along with the sample (e.g., mixed or co-injected). Exemplary internal standards include chondroitin/dermatan sulfate derived unsaturated disaccharides, e.g., —U-[1-3]-$Gal_{NAc,4S}$, —$U_{2S}$-[1-3]-$Gal_{NAc,4S}$, —U-[1-3]-$Gal_{NAc4S,6S}$. Other compounds suitable for use as internal standards include $\Delta U_{2S}$ hexosamine, adenosine 3',5'-diphosphate sodium salt (PAP), adenosine 3'-monophosphate sodium salt (AMP), and oligonucleotides such as polyuridines 5'-rUrUrUrUrU-3' (5-mer), 5'-rUrUrUrUrUrU-3' (6-mer), 5'-rUrUrUrUrUrUrUrUrUrUrUrUrUrU-3' (15-mer), and 5'-rUrUrUrUrUrUrUrUrUrUrUrUrUrUrUrUrUrUrUrU-3' (20-mer).

Additional information useful for the methods described herein can be found in, e.g., Linhardt et al. (1988) Biochem. J., 254:781-787 and Yates et al. (2004) J. Med. Chem., 47:277-280.

EXAMPLES

Example I

Analysis of Enoxaparin Using FPLC

FPLC was performed to analyze various enoxaparin samples as well as to provide a tetrasaccharide, hexasaccharide or octasaccharide fraction for further analysis, e.g., by HPLC. Chromatographic separation was performed by size exclusion using an Xk26/88 cm column packed with Superdex 30 resin using an AKTA purifier FPLC system. 50 mg of an enoxaparin sample was loaded onto the column for each run.

Example II

Chain Profile Analysis of Size-Separated Tetra- and Octasaccharide Fractions of Enoxaparin by SAX-HPLC Dry powder of tetrasaccharide fractions were reconstituted in water to a final concentration of 2 mg/mL and then analyzed with Propac PA1 (4.6×250 mm, 5 μm) column with a gradient of 0.2M and 2.0M NaCl solutions at a pH of 7.0. Column temperature and sample tray were kept at 25° C. and 4° C., respectively. Elution was monitored at 232 nm at a flow rate of 1.0 ml/min. Chain profiling of a tetrasaccharide fraction from enoxaparin on Propac PA1 column are given in FIG. 1.

Example III

Figure 2:
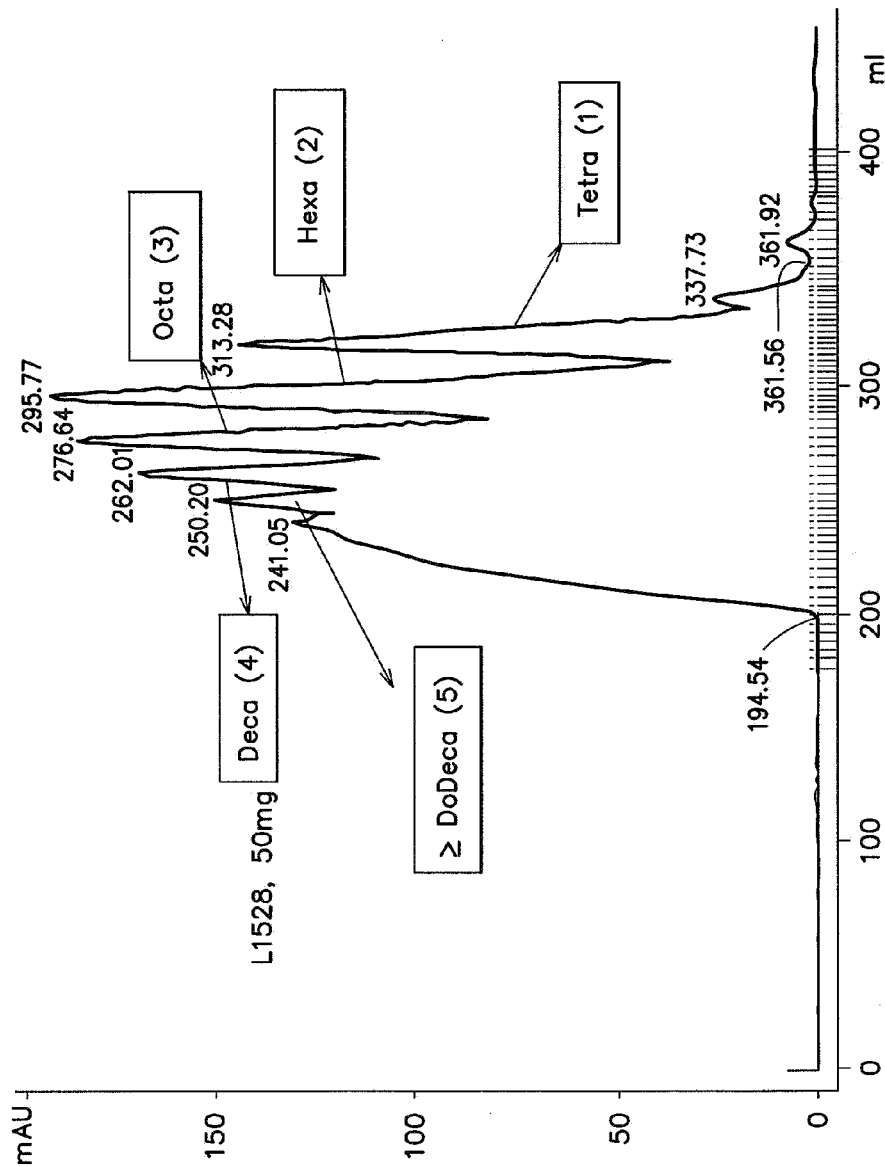
FIG. 2 is a trace of UV absorbance of 232 nm of FPLC analysis of an enoxaparin preparation. Each of the peaks representing the dodecasaccharide, decasaccharide, octasaccharide, hexasaccharide and tetrasaccharide fractions is labeled accordingly.
Figure 3:
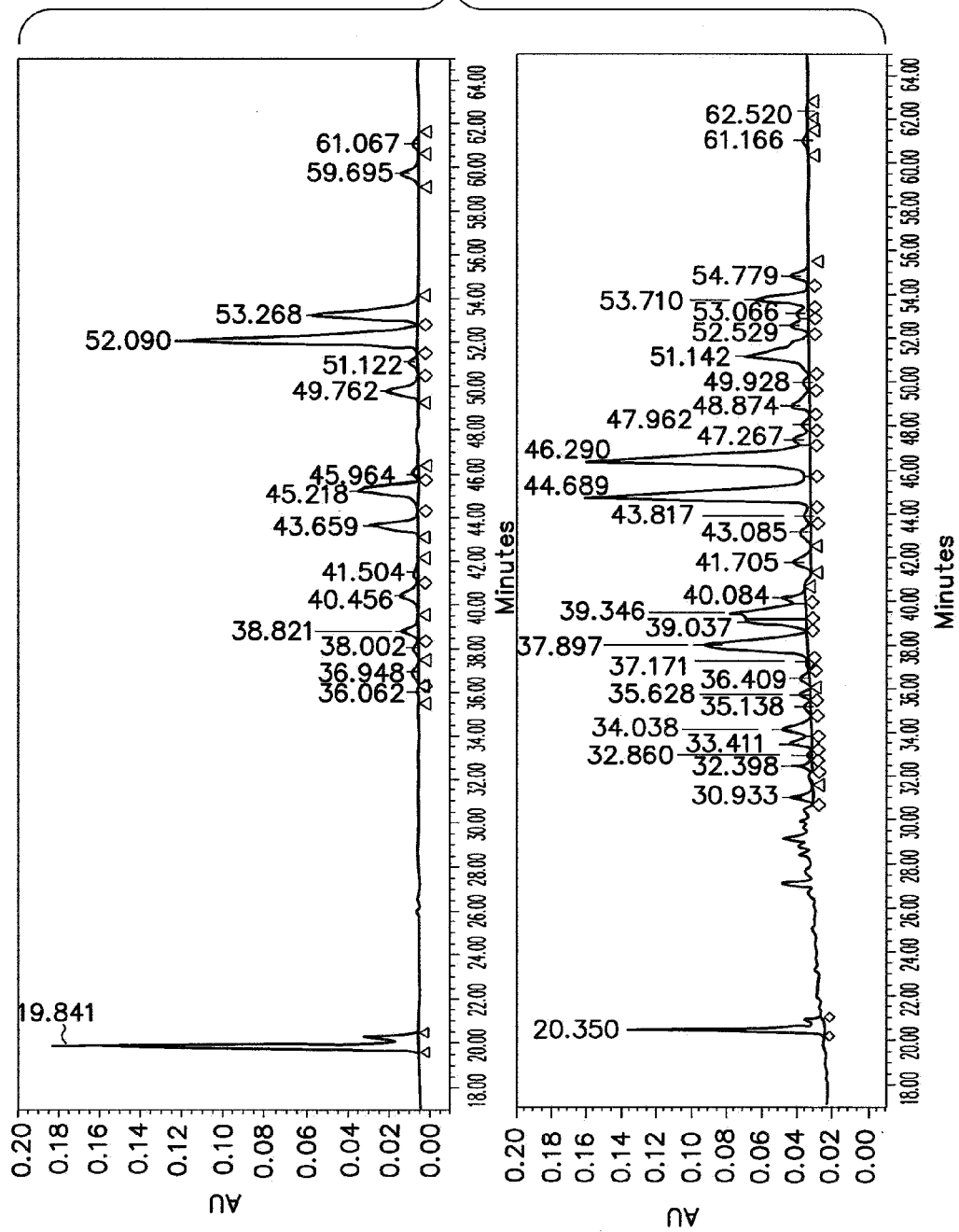
FIG. 3 is a trace of UV absorbance at 232 nm of a SAX-HPLC analysis of tetrasaccharide chains for (A) Lovenox® and (B) a non-equivalent Enoxaparin preparation. The peak in red at ~20 minutes is an internal standard.

Chain Profile Analysis of Size-Separated Hexasaccharide Fractions of Enoxaparin by CTA-SAX-HPLC Octadecyl ($C_{18}$) bonded silica stationary phases which are dynamically coated with cetyltrimethylammonium have been introduced in recent years for the chromatographic separation and analysis of heparin oligosaccharide mixtures. To this extent, Hypersil BDS $C_{18}$ column (21×250 mm, 5 μm) is dynamically coated with 1 mM cetyltrimethylammonium hydrogensulfate in a certain water:methanol ratio at room temperature. Hexasaccharide size-separated enoxaparin fractions were analyzed using a gradient of 0.2 to 2.0 M NaCl at a pH of 2.5. Elution profile was monitored at 232 nm at a flow rate of 5.0 ml/min. Chain profiling of a hexasaccharide fraction from enoxaparin on CTA-SAX-HPLC column are given in FIG. 2.

HPLC separation of those tetrasaccharide mixtures can be performed on a ProPac column (250×4.0 mm) from Dionex. The mobile phase can be 0.2 M sodium chloride (Eluent A) and 2.0 M sodium chloride (Eluent B), with step-gradient and a flow-rate of 1.0 ml/min. The mobile phase pH can be adjusted to 7.0 with hydrochloric acid. The elution profiles can be monitored by absorbance at 232 nm. This will give good separation. In addition to the major peak fully sulfated tetrasaccharide, numerous addition minor peaks, corresponding to undersulfated and modified structures which are unique for enoxaparin process can be observed.

Example IV

Chain Profile Analysis of Size-Separated Octasaccharide Fractions of Enoxaparin by SAX-HPLC Dry powder of octasaccharide fractions were reconstituted in water and then analyzed with Propac PA200 (9.0×250 mm, 5 μm) column with a gradient of 0.2M and 2.0M NaCl solutions. Column temperature and sample tray were kept at 25° C. and 4° C., respectively. Elution was monitored at 232 nm at a flow rate of 1.0 ml/min.

The references, patents and patent applications cited herein are incorporated by reference. Modifications and variations of these methods and products thereof will be obvious to those skilled in the art from the foregoing detailed description and are intended to be encompassed within the scope of the appended claims.

What is claimed:
1. A method of manufacturing an enoxaparin preparation comprising:
   esterification of carboxylate groups on uronic acid residues of a heparin preparation followed by beta-elimination to provide a LMWH preparation;
   providing a high performance liquid chromatography (HPLC) determination of whether a tetrasaccharide structure is present in the LMWH preparation in an amount provided in the following table:

| Peak # | Tetrasaccharide | Range A % Area under HPLC curve | | Range B % Area under HPLC curve | | Range C % Area under HPLC curve | |
|---|---|---|---|---|---|---|---|
| 1 | $\Delta UH_{NS6S}I_{2S}H_{NS6S}$ | 0.1 | 0.6 | Present or Detectable | | Present or Detectable | |
| 2 | $\Delta UH_{NS6S}I_{2S}H_{NS6S}$ $\Delta U_{gal}H_{NS6S}I_{2S}Man_{NS6S}$ | 0.6 | 1.2 | 0.6 | 1.2 | 0.4 | 1.4 |
| 3 | $\Delta U_{2S}H_{NS6S}I_{2S}H_{NS}$ (α) | 0.6 | 1.2 | 0.4 | 1.0 | 0.2 | 1.2 |
| 4 | $\Delta U_{2S}H_{NS6S}I_{2S}H_{NS}$ (β), $\Delta U_{2S}H_{NS6S}I_{2S}Man_{NS6S}$ (β) | 1.8 | 3.6 | 1.7 | 4.1 | 0.9 | 4.9 |
| 5 | $\Delta U_{2S}H_{NS6S}I_{2S}Man_{NS}$ (α), $\Delta U_{2S}H_{NS}I_{2S}H_{NS6S}$ (α) | 2.1 | 3.7 | 2.2 | 4.0 | 1.6 | 4.6 |
| 6 | $\Delta U_{2S}H_{NS}I_{2S}H_{NS6S}$ (β) | 0.5 | 1.6 | 0.4 | 1.6 | 0.0 | 2.0 |
| 7 | $\Delta U_{2S}H_{NS6S}I_{2S}Man_{NS}$ (1,6 anhydro) | 5.9 | 9.0 | 5.6 | 9.2 | 4.4 | 10.4 |
| 8 | $\Delta U_{2S}H_{NS6S}I_{2S}H_{NS}$ (1,6 anhydro) | 7.0 | 9.9 | 6.6 | 10.2 | 5.4 | 11.4 |
| 9 | $\Delta U_{2S}H_{NS6S}G_{2S}H_{NS}$ (α) | 0.9 | 1.6 | 0.8 | 1.4 | 0.6 | 1.6 |
| 10 | $\Delta U_{2S}H_{NS6S}GH_{NS6S}$ (α) | 5.0 | 6.2 | 4.9 | 6.7 | 4.3 | 7.3 |
| 11 | $\Delta U_{2S}H_{NS6S}GMan_{NS6S}$ (α, β) | 1.2 | 1.9 | 1.0 | 2.2 | 0.6 | 2.6 |
| 12 | $\Delta U_{2S}H_{NS6S}I_{2S}H_{NS6S}$ (α), $\Delta U_{2S}H_{NS6S}I_{2S}Man_{NS6S}$ (β) | 39.7 | 48.0 | 38.1 | 48.9 | 34.5 | 52.5 |
| 13 | $\Delta U_{2S}H_{NS6S}I_{2S}H_{NS6S}$ (β), $\Delta U_{2S}H_{NS6S}I_{2S}Man_{NS6S}$ (α) | 18.1 | 20.7 | 17.8 | 20.8 | 16.8 | 21.8 |
| 14 | $\Delta U_{2S}H_{NS6S}G_{2S}H_{NS6S}$ (α) | 2.3 | 4.0 | 1.9 | 4.3 | 1.1 | 5.1 |
| 15 | $\Delta U_{2S}H_{NS6S}G_{2S}H_{NS6S}$ (β) | 0.6 | 1.4 | 0.4 | 1.6 | 0.0 | 2.0 | and
   if said structures are present in an amount provided in the table, processing said preparation into an enoxaparin drug product to thereby manufacture an enoxaparin preparation.

2. The method of claim 1, wherein processing further includes one or more of: selecting, accepting, shipping, labeling, packaging, or selling said preparation.

3. The method of claim 2, wherein processing includes formulating said preparation.

4. The method of claim 2, wherein processing includes labeling said preparation.

\* \* \* \* \*